US010149919B2

(12) United States Patent
Chisholm et al.

(10) Patent No.: US 10,149,919 B2
(45) Date of Patent: Dec. 11, 2018

(54) HARDENABLE MULTI-PART ACRYLIC COMPOSITION

(71) Applicant: Lucite International Speciality Polymers & Resins Limited, Southampton, Hampshire (GB)

(72) Inventors: Michael Stephen Chisholm, Newton (GB); Sera Saheb Abed-Ali, Aycliffe (GB)

(73) Assignee: LUCITE INTERNATIONAL SPECIALTY POLYMERS & RESINS LIMITED, Southampton, Hampshire (GB)

( * ) Notice: Subject to any disclaimer, the term of this patent is extended or adjusted under 35 U.S.C. 154(b) by 50 days.

(21) Appl. No.: 15/026,111

(22) PCT Filed: Sep. 30, 2014

(86) PCT No.: PCT/GB2014/052950
§ 371 (c)(1),
(2) Date: Mar. 30, 2016

(87) PCT Pub. No.: WO2015/044689
PCT Pub. Date: Apr. 2, 2015

(65) Prior Publication Data
US 2016/0243274 A1 Aug. 25, 2016

(30) Foreign Application Priority Data
Sep. 30, 2013 (GB) .................................. 1317299.4

(51) Int. Cl.
A61L 24/06 (2006.01)
A61K 6/083 (2006.01)
A61L 27/16 (2006.01)
A61L 27/50 (2006.01)
A61L 24/00 (2006.01)
C08F 265/06 (2006.01)
C08L 33/12 (2006.01)
C08L 33/14 (2006.01)
C08F 292/00 (2006.01)
C08K 3/30 (2006.01)

(52) U.S. Cl.
CPC ............ *A61L 24/06* (2013.01); *A61K 6/0835* (2013.01); *A61L 24/001* (2013.01); *A61L 27/16* (2013.01); *A61L 27/50* (2013.01); *C08F 265/06* (2013.01); *C08F 292/00* (2013.01); *C08K 3/30* (2013.01); *C08L 33/12* (2013.01); *C08L 33/14* (2013.01); *A61L 2430/02* (2013.01); *C08K 2003/3045* (2013.01)

(58) Field of Classification Search
USPC ......................... 523/117, 210, 333
See application file for complete search history.

(56) References Cited

U.S. PATENT DOCUMENTS

| 4,093,576 | A | 6/1978 | DeWijn |
| 4,500,658 | A | 2/1985 | Fox |
| 4,791,150 | A | 12/1988 | Braden et al. |
| 5,795,922 | A | 8/1998 | Demian et al. |
| 2009/0239970 | A1* | 9/2009 | Rodrigues .......... A61B 17/7095 523/117 |
| 2011/0054392 | A1 | 3/2011 | Nies |
| 2012/0195848 | A1 | 8/2012 | Lu et al. |

FOREIGN PATENT DOCUMENTS

| EP | 0218471 A1 | 4/1987 |
| EP | 2139530 B1 | 3/2008 |
| JP | H0624927 A | 2/1994 |
| RU | 2010104643 A | 8/2011 |
| TW | 201012863 A | 4/2010 |

(Continued)

OTHER PUBLICATIONS

International Search Report for PCT/GB2014/052950 dated Apr. 12, 2014 (3 pages).
Andreas Boger et al., "Properties of an Injectable Low Modulus PMMA Bone Cement for Osteoporotic Bone", Journal of Biomedical Materials Research Part B: Applied Biomaterials, vol. 86B, Part 2, p. 472-482 (2008).
J.R. de Wijn, "Poly(methyl methacrylate)-aqueous phase blends: In situ curing porous materials", J. Biomed. Res. Symposium, No. 7, p. 625-634 (1976) (Abstract) (2 pages).
English Translation of Russian Office Action dated Jul. 20, 2018 for Russian Application No. 2016116938 (8 pages).
English Translation of Russian Search Report dated Jul. 20, 2018 for Russian Application No. 2016116938 (3 pages).

*Primary Examiner* — Tae H Yoon
(74) *Attorney, Agent, or Firm* — Shumaker, Loop & Kendrick, LLP

(57) ABSTRACT

The invention relates to a hardenable multi-part liquid acrylic composition. The composition comprises a storage stable liquid first part, a storage stable liquid second part and optionally, a third or further liquid parts. The parts are operable to form a cement which hardens to a solid upon mixing of the parts together. The composition comprises an acrylic monomer component, an initiator component, acrylic polymer particles and a radiopacifying filler. The initiator component is present in an amount of effective to polymerize the acrylic monomer component upon being mixed and/or activated therewith. At least some of the radiopacifying filler is encapsulated within and/or adsorbed on the acrylic polymer particles in a liquid part. The invention extends to an at least twin barreled syringe or caulking gun accommodating the multi-part composition, a method of producing the multi-part composition, a composition for use as bone cement composition or in dental repairs, a liquid composition comprising a first sub-population of emulsion or non-emulsion polymerized acrylic polymer particles and radiopacifying filler encapsulated and/or adsorbed in the first sub-population of acrylic polymer particles and bone cement compositions or dental compositions.

42 Claims, No Drawings

(56) References Cited

FOREIGN PATENT DOCUMENTS

| WO | 1998/24398 A1 | 6/1998 |
| WO | WO 2096474 * | 12/2002 |
| WO | 2004/071543 A1 | 8/2004 |
| WO | 2009108893 A2 | 9/2009 |
| WO | 2009108893 A3 | 9/2009 |
| WO | 2010/005442 A1 | 1/2010 |
| WO | 2010018412 A1 | 2/2010 |
| WO | 2013/144590 A1 | 10/2013 |

* cited by examiner

HARDENABLE MULTI-PART ACRYLIC COMPOSITION

CROSS-REFERENCE TO RELATED APPLICATION

This U.S. National Stage Application claims priority from PCT/GB2014/052950 filed Sep. 30, 2014, which claims priority from GB 1317299.4 filed Sep. 30, 2013, the entirety of which are incorporated herein by reference.

TECHNICAL FIELD AND BACKGROUND OF THE INVENTION

The present invention relates to a hardenable multi-part liquid acrylic composition comprising a radiopacifying filler, in particular but not exclusively, an acrylic composition which has at least two liquid parts which react with each other upon being mixed together to form a cement such as a bone cement which hardens to a solid, an at least twin barreled syringe or caulking gun accommodating the multi-part composition and a method of producing the multi-part composition.

Hardenable compositions formed by mixing together acrylic polymers and monomers are useful in a wide range of applications. Particular utility is found in dental, medical, adhesive and construction applications, where such materials have been used for over 40 years.

Dental applications include denture bases, denture base plates, denture liners, denture repairs, custom trays, veneering for crowns and bridgework, artificial teeth, veneers and repair for natural teeth and tooth restorative fillings. Medical applications include bone cements for bone cavities such as prosthetic cements, cranial cements and vertebral cements in vertebroplasty and kyphoplasty. Further applications include the production of shaped articles that harden extra-corporeally and which can then be introduced into the body.

Hardenable acrylic compositions are generally composed of a solid component and a liquid component. The solid component comprises a powder formed from polymer particles and, if appropriate, further additives, such as polymerization initiators and catalysts, fillers, pigments and dyestuffs. The liquid component comprises a liquid monomer or monomers and further additives, such as accelerators and stabilisers. When ready for use, the solid and liquid components are mixed together to form a liquid or semi-solid paste, which, under the action of the polymerization initiators and accelerators, increases in viscosity and hardens into a solid.

However, research has also been undertaken in relation to liquid first and second parts. Such two part compositions may permit easier mixing of the two parts. WO98/24398 (Lautenschlager et al) describes a bone cement system of low porosity prepared by mixing together two liquid components. Each liquid component consists of solutions of PMMA in MMA monomer, with one solution containing an initiator (e.g., BPO) and the other solution containing an activator (e.g. DMPT). This system has the disadvantages of limited storage stability, a relatively high polymerization exotherm and an increased shrinkage that is produced by the necessarily higher levels of MMA that are required to prepare the solutions. WO2010/005442 (Hasenwinkel et al) attempts to overcome some of these disadvantages by incorporating cross-linked PMMA beads into the solutions. However, the disadvantage of limited storage stability remains.

US2011/0054392 and EP 2,139,530 (Nies) describe an implant material for improved release of active ingredients comprising two components. The first component comprises a mixture of polymer powder and BPO initiator that is made into a stable non-settling paste by adding water, surface active agent (e.g. Tween 80) and a water soluble polymer (e.g., carboxymethyl starch). The second component comprises a solution of PMMA dissolved in MMA monomer plus DMPT accelerator. Each component is charged to separate compartments of a double chamber syringe and mixed by pressing through a static mixer. The high water content provides high porosity in the final hardened product facilitating the improved release of active ingredients. However, the relatively high porosity (typically approximately 16% and higher) creates the disadvantage of reduced mechanical properties in the final cement, such as a reduced compression strength that is less than acceptable for conventional bone cements.

Additional prior art documents De Wijn, J. Biomed. Mater. Res. Symposium, No 7, pp 625-635 (1976), U.S. Pat. No. 4,093,576, Boger et al., J. Biomed. Mat. Res. Part B: Applied Biomaterials, volume 86B, part 2, pp 474-482 (2008) and WO2004/071543 discuss the inclusion of water in a bone cement system, but not for the purpose of delivery via a double chamber syringe and mixing by pressing through a static mixer.

De Wijn in J. Biomed. Mater. Res. Symposium, No 7, pp 625-635 (1976) and in U.S. Pat. No. 4,093,576 describes mixing of a conventional polymer powder with a gelling agent in powder form, e.g. carboxymethylcellulose (CMC). Monomer is then added to form a cement dough, followed by the addition of water to produce gelling with the CMC. The resultant mixture is then cured to form a porous material. The open pore structure of the porous material is said to allow for tissue invasion over time to further anchor the implant with surrounding connective tissue or bone. However, the porous nature of the material again creates the disadvantage of reduced mechanical properties compared to conventional bone cements.

Boger et al in J. Biomed. Mat. Res. Part B: Applied Biomaterials, volume 86B, part 2, pp 474-482 (2008) and Bisig et al in WO2004/071543 describe an injectable low modulus PMMA bone cement for osteoporotic bone. This system consists of three components, namely the powder and liquid components of a conventional two-component bone cement, plus an aqueous solution of hyaluronic acid. Porous materials result that are claimed to have mechanical properties close to that of human cancellous bone, significantly lower than the mechanical properties of conventional bone cement.

Radiopacifying fillers such as barium sulphate may traditionally be added to a solid-liquid bone cement composition in either the first or second part, or both. However, the introduction of filler particles has a tendency to also reduce the mechanical properties of the hardened composition such as flexural, tensile and fatigue properties. Accordingly, introducing radiopacifying filler into liquid—liquid two part compositions also presents significant mechanical property issues.

A further problem arises when mixing a liquid first part and a liquid second part such as through a static mixer connected to twin compartments of a syringe or caulking gun if the viscosity of one or both of the liquids is too high or the viscosity of the liquids are significantly different to each other.

One solution to the problem is to reduce the viscosity of a higher polymer content liquid part and match it more closely to the viscosity of the lower polymer or monomer containing liquid part.

The viscosity could be reduced by increasing the amount of liquid carrier (e.g. water) in the liquid part. However, higher levels of water in the reacted two part acrylic composition increase the amount of porosity and therefore also reduce the mechanical properties in the final bone cement. Radiopacifying fillers tend to increase viscosity still further exacerbating this viscosity problem when they are used.

U.S. Pat. No. 4,500,658 discloses that a problem with certain types of metal filler such as lead foil, silver alloy, gold and 1% set amalgam are that they cause stress concentrations at the interface between the insert and the resin which weakens and fractures the material.

On the other hand, heavy metal compounds externally attached to the beads are inconvenient. In addition, it is pointed out that high levels of barium sulphate are necessary in the resin to render it radiopaque but that at these levels there is a negative impact on the strength of the material. The document describes that the filler can be encapsulated and uniformly dispersed in the bead using suspension polymerisation. The beads are said to be useful in biomedical applications to colour biomedical materials and devices. An example is proposed of compounding the bead particles into a dry powder for a solid-liquid denture composition. The beads may be ground up prior to use in a composition. The mixtures with monomer disclosed imply that most of the bead is dissolved in the monomer thereby allowing encapsulated radioopaque pigment to disperse in the monomer. Accordingly, the document merely teaches a manner of opacifer delivery to the matrix of the final polymer. However, no mention is made of using the bead particles in a liquid-liquid system or any advantages in so doing. EP0218471 teaches that barium sulphate radiopacifier incorporated into ethylmethacrylate beads can give improved mechanical properties with n-butyl methacrylate monomer in a solid liquid system. There is no mention of the possibility to reduce the concentration of radiopacifying filler particles through encapsulating within acrylic polymer bead particles, nor do they mention any effect on viscosity of a liquid-liquid bone cement system as it is only used as the component of a bone cement powder. Furthermore, upon mixing the bead polymer is said to be almost fully dissolved in monomer so that there is no intention to maintain encapsulation in the final product.

SUMMARY OF THE INVENTION

It is one or more of the objects of the present invention to provide a solution(s) to one or more of the above problems.

Surprisingly, a hardenable liquid-liquid multi-part composition and methods of production thereof have been discovered that introduce radiopacifying filler without significantly affecting mechanical properties in the hardened composition and which also do not significantly increase the viscosity of the radiopacifier containing liquid part without resorting to detrimental methods such as increasing the amount of water as a liquid carrier.

Advantageously, therefore, compositions are provided with improved mechanical properties such as improved flexural, tensile and fatigue properties.

DETAILED DESCRIPTION

According to a first aspect of the present invention there is provided a hardenable multi-part acrylic composition comprising a storage stable liquid first part, a storage stable liquid second part and optionally, a third or further liquid parts, the parts being operable to form a cement which hardens to a solid upon mixing of the parts together, the composition comprising an acrylic monomer component, an initiator component, acrylic polymer particles and a radiopacifying filler, the initiator component being present in an amount effective to polymerize the acrylic monomer component upon being mixed and/or activated therewith characterized in that at least some of the radiopacifying filler is encapsulated within and/or adsorbed on the acrylic polymer particles in a liquid part.

As indicated, the composition may include more than two parts for instance the initiator component could be stored in a separate third part but for convenience the multi-part acrylic composition of any of the aspects of the invention herein is typically only a two-part composition i.e. there is no third or further part.

The acrylic polymer particles may comprise two or more sub-population(s) of acrylic polymer particles. A sub-population may be generally distinguishable from the other sub-population(s) by one or more properties such as molecular weight (MW), molecular weight distribution, porosity, the nature and distribution of the (co)monomer residues, particle size, particle size distribution, and/or type, the presence or absence of residual initiator and, if present, the amount and type of residual initiator. If there are two or more sub-populations of acrylic polymer particles they may therefore be of one or more types for example suspension polymerized, emulsion polymerized, solution polymerized and/or batch polymerized. Typically, if suspension, bulk or solution polymerized the sub-population(s) are present as polymer beads and if emulsion polymerized the sub-population(s) are present as emulsion particles which may be coalesced together, agglomerated together or independent.

The storage stable liquid first part and storage stable liquid second part are preferably stored and reacted between 0 and 30° C., more preferably, between 18 to 25° C., most preferably, between 20 to 23° C. and in any case typically under normal atmospheric pressure ranges. The preparation of a cement from the mixing of the liquid first part and the liquid second part can be carried out in various ways that will be appreciated by those skilled in the art, for example by hand mixing or by injection of the separate parts through a static mixer.

Typically, the initiator component is present in an amount effective to fully polymerize the monomer component. For example, to at least polymerize 85% w/w of the monomer component, more typically, at least 90% w/w, most typically, 95%-98% w/w of the monomer component. In addition, the initiator component may be present in excess of the amount that would be effective to fully polymerize the monomer component.

Acrylic polymer particles with encapsulated and/or adsorbed radiopacifying filler may be present in a liquid carrier in the liquid first part and/or liquid second part. The liquid carrier may be water or other liquid such as monomer, organic solvent, plasticizer, liquid polymer, diluent, more typically, water or acrylic monomer.

In this respect, it will be appreciated that the acrylic monomer of the invention is generally present as a liquid and that therefore, the acrylic monomer may be the liquid carrier for acrylic polymer particles and radiopacifying filler. However, in a preferred aspect of the invention, the liquid carrier for the acrylic polymer particles and encapsulated and/or adsorbed radiopacifying filler is other than monomer, more preferably, a substantially non-solvating carrier for the acrylic polymer particles with encapsulated and/or adsorbed radiopacifying filler, most preferably, water. Therefore, according to the characterizing portion of any aspect of the present invention, preferably, at least some of the radiopacifying filler is encapsulated within and/or adsorbed on the acrylic polymer particles in suspension in a liquid part.

By suspension is meant in a non-solvated form and includes dispersions and emulsions.

In this respect, it is possible for the liquid part to be the acrylic monomer component if this is saturated with polymer such that acrylic polymer particles can be suspended therein without solvation, however, generally, a non-solvating liquid carrier is utilized for the acrylic polymer particles with encapsulated and/or adsorbed radiopacifying filler.

Typically, at least 25% w/w of the total radiopacifying filler present in the composition and therefore, typically, also in the final hardened composition, is encapsulated within and/or adsorbed on acrylic polymer particles, more typically, at least 50% w/w, most typically, at least 75% w/w is so encapsulated and/or adsorbed.

Therefore, between 20 and 100% w/w of the radiopacifying filler in the composition and therefore, typically, also in the final hardened composition, is encapsulated within and/or adsorbed on acrylic polymer particles, more typically, between 30% and 100% w/w, most typically, between 60 and 100% w/w. Although it is preferred for the level of encapsulated and/or adsorbed radiopacifying filler to be maintained in the final hardened composition there may nevertheless be some dissolution of the carrier particle in the monomer and accordingly, in the alternative, the level of the radiopacifying filler in the final hardened composition which is encapsulated within and/or adsorbed on acrylic polymer particles is between 10 and 100% w/w, more typically, between 20% and 95% w/w, most typically, between 50 and 90% w/w.

Typically, the level of radiopacifying filler in the hardenable multi-part composition of the invention is between 1 and 50% w/w, more typically, between 5 and 40% w/w most typically, between 6.5 and 30% w/w. Preferably, the radiopacifying filler is present at the composition levels specified encapsulated within or adsorbed on the acrylic polymer particles. Typically, the radiopacifying filler is present at or around the compositional levels specified encapsulated within or adsorbed on the acrylic polymer particles in the hardened cement i.e. the fully polymerised product. Accordingly, the encapsulated and or adsorbed radiopacifying filler should preferably not be released into the matrix monomer and is therefore typically present at the composition levels specified in or on acrylic polymer particles in suspension in a liquid part of the hardenable composition. However, during mixing some of the adsorbed radiopacifying filler may migrate into the monomer and, in addition, some of the polymer particle may dissolve thus releasing radiopacifying filler into the matrix monomer. Accordingly, the level of encapsulated radiopacifying filler present in the final hardened cement may be reduced from the compositional levels above by up to 40%, more typically, by up to 20%.

Advantageously, a high level of encapsulation in the final hardened product is also achieved by incorporating one or more sub-population(s) of acrylic polymer particles into the composition having a lower average particle size than the average particle size of the sub-population(s) having encapsulated and/or adsorbed radiopacifying filler. The average particle size of these lower average particle size acrylic polymer particles is typically <30 μm, more typically <20 μm, most typically <10 μm. Typical lower average particle size sub-population ranges being 0.01-30 μm, more typically, 0.02-20 μm, most typically, 0.1-10 μm. Such lower average particle size sub-populations may be present in any of the liquid parts of the hardenable composition but are generally kept apart from the monomer so that they preferentially dissolve in the monomer after mixing thereby preventing or reducing dissolution of the sub-population(s) having encapsulated and/or adsorbed radiopacifying filler. Accordingly, the larger average particle size acrylic polymer particles with encapsulated and/or adsorbed radiopacifying filler do not dissolve or do not dissolve to the same extent in the monomer as the lower average particle size sub-population(s).

Accordingly, when emulsion particles, the Z-average particle size of the lower average particle size sub-population(s) is preferably in the range 0.01 to 2 μm, more preferably, 0.02 to 1 μm, most preferably, 0.05 to 0.5 μm, especially, 0.1 to 0.45 μm.

When bead particles, the mean particle size of the lower average particle size sub-population(s) is preferably, in the range 1-30 μm, more preferably, 2-20 μm, most preferably, 2.5-15 μm.

Although any acrylic polymer particle may be used as the lower average particle size sub-population(s), it is preferred that emulsion particles as defined herein are used.

The average particle size of the sub-population(s) having encapsulated and/or adsorbed radiopacifying filler is preferably in the range 10 to 1000 μm, more preferably, 20 to 600 μm, most preferably, 25 to 200 μm. Generally, in such ranges this should be taken to refer to mean particle size.

Generally, herein the average particle size is determined by a technique appropriate to the size of the particle being characterised. Accordingly, a lower average particle size sub-population may have its average particle size characterised by a different technique than the sub-population it is being compared with. Nevertheless, this is appropriate where the average particle sizes of the relevant sub-populations are clearly distinguishable. Where the average particle size is relatively close it may be appropriate to use only the same technique. For instance, sub micron particles may be characterised by their Z-average particle size whereas particles >10 μm can be characterised by their mean particle size. Particles between 1 and 10 μm could be characterised by either measurement and if both sub-populations for comparison fall in this range then the same technique should be adopted. Accordingly, herein, emulsion particles are preferably characterised by their Z-average particle size and bead particles are preferably characterised by their mean particle size.

Preferably, the lower average particle size sub-population particle size is sufficiently lower than the sub-population having encapsulated and/or adsorbed radiopacifying filler particle size to retard dissolution of the latter in monomer. Preferably, the average particle size is at least 10% lower than the average particle size of the larger particle.

Notwithstanding the above, it is also possible for some radiopacifying filler to be present in the composition and/or hardened cement in a form that is not encapsulated and/or adsorbed in or on acrylic polymer particles, for example in the liquid first part and/or liquid second part. This is either independently added radiopacifying filler or radiopacifying filler that has migrated from an encapsulated or adsorbed form into the surrounding liquid.

Where there are two or more sub-populations of acrylic polymer particles, the encapsulated and/or adsorbed radiopacifying filler may be encapsulated and/or adsorbed in only one sub-population or in more than one sub-population of acrylic polymer particles. If the sub-populations extend to more than one type of acrylic polymer particle, the radiopacifying filler may be present in any type. Preferably, however, the radiopacifying filler is encapsulated within and/or adsorbed on polymer beads or in two or more bead sub-populations.

Preferably, at least 90% w/w of the total acrylic monomer component in the composition is present in the liquid second part, more preferably, at least 95% w/w, most preferably, at least 99% w/w. In preferred embodiments, substantially all the acrylic monomer component in the composition is present in the liquid second part. Typically, therefore, the acrylic monomer component is present in only one part of the composition. Typically, the acrylic monomer component containing liquid part includes acrylic polymer particles dissolved therein.

Typically, all or substantially all of the said acrylic monomer component and the said initiator component are located in separate parts of the said multi-part composition so that the part containing the monomer component is storage stable to polymerisation.

The sub-populations of acrylic polymer particles may include one or more sub-populations of acrylic polymer beads and one or more sub-populations of emulsion polymerized acrylic polymer particles. Alternatively, the particles may also be crushed, milled, or ground bulk polymerized acrylic polymer or crushed, milled, or ground acrylic polymer beads.

Preferably, where there are two or more sub-populations, the radiopacifying filler is encapsulated and/or adsorbed in only one sub-population of acrylic polymer particles but it may be encapsulated and/or adsorbed in more than one sub-population as mentioned above. Typically, the radiopacifying filler is only encapsulated within and/or adsorbed on acrylic polymer beads but it may alternatively only, or additionally, be encapsulated in and/or adsorbed on emulsion polymerized acrylic polymer particles and in either case in the first and/or second part. Typically, it is convenient to encapsulate and/or adsorb the radiopacifying filler in only one part of the composition, preferably, the first part thereof. If radiopacifying filler is encapsulated and/or adsorbed in only one sub-population type of acrylic polymer particle further sub-population types of acrylic polymer particles may still be present in the composition. For instance, if the radiopacifying filler is encapsulated and/or adsorbed in the emulsion polymerized acrylic polymer particles or acrylic polymer beads, both types of particles may still be present in the composition. In preferred embodiments, the acrylic polymer particles include acrylic polymer beads in both the first and second parts and emulsion polymerized acrylic polymer particles in the liquid first part and radiopacifying filler may be encapsulated and/or adsorbed in any one or more sub-populations of acrylic polymer particles. Preferably, however, the radiopacifying filler is only encapsulated and/or adsorbed in acrylic polymer beads, more preferably in acrylic polymer beads whether a sub-population or otherwise in the liquid first part.

Typically, at least 50% w/w of the total encapsulated and/or adsorbed radiopacifying filler in the composition is present in acrylic polymer beads, more typically, at least 90% w/w, most typically, at least 95% w/w is present in the acrylic polymer beads and more preferably at these levels in the acrylic polymer beads in the liquid first part. Especially preferred is for the filler to be present at these levels in such beads in suspension in the liquid part.

Encapsulation of the radiopacifying filler has the additional advantage of reducing the viscosity of the filled liquid part over the case where the radiopacifying filler is added as a separate component. For example, the viscosity may be reduced compared to a non-encapsulated radiopacifier equivalent system by 30% or more.

One method of encapsulation is to disperse the radiopacifying filler such as barium sulphate within acrylic monomer, then polymerize the monomer by, for example, bulk, emulsion or suspension polymerization, thereby encapsulating the radiopacifying filler within the resulting acrylic polymer particles. The preferred approach is to encapsulate the radiopacifying filler within bead polymer particles such as those produced by suspension polymerisation.

It has been surprisingly found that by encapsulating the radiopacifying filler within acrylic polymer particles, the concentration of radiopacifying filler particles in the continuous matrix formed by mixing the liquid first part and liquid second part is reduced, thereby reducing the number of stress concentrating defects in the continuous matrix. As a result, the normal reduction in mechanical properties that would occur if all the filler was to be found in the continuous matrix can be avoided. Further, by initially finely dispersing the radiopacifying filler in monomer and then encapsulating it within the acrylic polymer particle, it is possible to achieve the same radiopacifying effect through use of an even lower amount of filler. This leads to a further enhancement in mechanical properties. In addition, the viscosity of the liquid part is reduced thus facilitating better viscosity matching between the respective liquid parts, particularly if the radiopacifier is found in the liquid first part and the monomer component is found in the liquid second part.

Suitable radiopacifying fillers may be selected from the list comprising zirconium dioxide, strontium carbonate, powdered tantalum, powdered tungsten, barium sulphate and mixtures thereof. Preferably, the radiopacifying filler is barium sulphate. Typically, when the radiopacifying filler is barium sulphate, the barium sulphate is both encapsulated in and adsorbed on the acrylic polymer particles, more typically, bead polymer particles. On the other hand, for other radiopacifying fillers such as zirconium dioxide, the zirconium dioxide is generally only encapsulated.

By radiopacifying herein is meant the ability to render a material more distinguishable from surrounding material when subjected to X-rays.

In a preferred embodiment, the liquid first part comprises acrylic polymer particles present as polymer beads and having encapsulated and/or adsorbed radiopacifying filler. Typically, the liquid second part comprises the monomer component. Preferably, the composition of the invention comprises emulsion polymerized acrylic polymer particles. Typically, the emulsion polymerized acrylic polymer particles are dispersed in a liquid carrier.

In particularly preferred aspects of the present invention, the liquid part containing the acrylic polymer particles and encapsulated and/or adsorbed radiopacifying filler further contains the emulsion polymerized acrylic polymer particles. Preferably, the emulsion polymerized particles in the liquid carrier are in the form of an acrylic polymer emulsion dispersion. Preferably, the liquid carrier for the acrylic polymer particles, encapsulated and/or adsorbed radiopacifying filler and emulsion polymerized acrylic polymer particles is water.

Typically, therefore, the acrylic polymer emulsion provides a continuous phase for the liquid first part. Typically, the acrylic polymer emulsion consists of emulsion polymerized acrylic polymer particles, at least one emulsifier and water.

The invention extends in another aspect to a solid cement composition produced from mixing a multi-part acrylic composition according to any of the aspects herein. The invention further extends in another aspect to a syringe or caulking gun having at least two barrels comprising a liquid first part according to any aspect herein in a first barrel thereof and a liquid second part according to any aspect herein in the second barrel thereof and also optionally comprising further components as defined herein.

Advantageously, the invention is for use in the treatment of human or animal bone.

Furthermore, the invention extends in another aspect to compositions of the liquid first part of the invention for use as a dough time reduction agent in a hardenable multi-part acrylic composition.

According to a further aspect of the present invention there is provided a method of producing an acrylic cement from a multi-part acrylic composition according to any of the aspects of the present invention comprising the step of mixing the said first and second parts.

The above process may be a manual mixing process. However, use of an adapted syringe or caulking gun is preferred.

According to a further aspect of the invention there is provided a method of producing a hardenable multi-part acrylic composition according to any of the aspects of the present invention comprising the steps of:—
 (a) producing a storage stable liquid first part and a storage stable liquid second part according to the first aspect of the present invention;
  (i) wherein step (a) comprises the step of polymerizing an acrylic monomer composition to form acrylic polymer particles wherein the polymerisation is carried out in the presence of radiopacifying filler to thereby encapsulate the radiopacifying filler in acrylic polymer particles.

As indicated, the composition may include emulsion polymerised acrylic particles. These may be made in accordance with techniques known to those skilled in the art. However, preferred features of production include:—
 emulsion polymerizing at least one acrylic monomer composition optionally in the presence of radiopacifying filler to produce an acrylic polymer emulsion optionally with encapsulated and/or adsorbed radiopacifying filler; and/or
 suspension, bulk or solution polymerizing at least one acrylic monomer composition optionally in the presence of radiopacifying filler to produce an acrylic polymer bead particle optionally with encapsulated and/or adsorbed radiopacifying filler.

Preferably, therefore, the composition includes an acrylic polymer emulsion or a modified acrylic polymer emulsion modified by combination with further acrylic polymer particles or further components of the composition which in any case provides a liquid carrier for the acrylic polymer particles suspended therein in the liquid part so that the normally solid powder acrylic polymer particle component of the composition is instead provided as a storage stable liquid. Accordingly, the liquid phase of the emulsion may have bead type polymer particles in addition to emulsion particles independently suspended therein and optionally further components of the composition such as initiator and/or accelerator. Advantageously, therefore, the acrylic polymer particles may be present as bead polymer particles and emulsion polymer particles in a liquid carrier giving the possibility of encapsulation of radiopacifier in either bead polymer particles, emulsion polymer particles or both. If present, the emulsion polymerized acrylic particles are preferably microparticles.

Additionally, given that monomer is already in a liquid form, through use of the emulsion polymerized acrylic particles directly as prepared in their primary emulsion form, the additional benefit is provided in of being able to store and deliver each component of the hardenable composition as a liquid such as an emulsion, modified emulsion, dispersion, paste or solution within separate compartments of a double chamber syringe or caulking gun. These components can then be conveniently mixed and delivered directly to the required site as required by pressing in tandem through a mixing tip applied to the syringe/caulking gun such as a static mixer or helical mixer applied to the syringe/caulking gun, thereby overcoming the inconvenience of manual mixing. In addition, the mixing of the hardenable composition is more reproducible, safer and reliable.

Furthermore, storing the individual components in respective chambers of a double chamber syringe or caulking gun provides the benefits of avoiding the risk encountered in manual mixing of exposure to hazardous monomers by operators. Mixing is achieved directly during application of the cement to the desired site.

In addition, it is also possible in some embodiments to provide a disposable mixing tip so that the double chamber syringe or caulking gun may be used on more than one occasion by attaching a further mixing tip. Double chambers have not hitherto been possible because conventional powder cannot be pushed out into the nozzle. Therefore, it is necessary to mix the powder and liquid components prior to placement in a single chamber syringe. Such a mixture is not storage stable so the option of later re-using the barrel of material with a replacement mixing tip head was not possible.

A further advantage of the invention is that the components of the multi-part composition have long storage stability.

A further advantage to the invention is that the emulsion polymerized acrylic particles can be used directly in a liquid emulsion or bead polymer modified liquid emulsion to produce a hardenable composition with shortened dough time without having to produce a network of coalesced emulsion polymerized microparticles formed by drying of the liquid emulsion to form a powder. This therefore saves significant energy costs and improves manufacturing efficiency.

The multi-part hardenable compositions of the invention also attain a low maximum exotherm temperature during hardening thus avoiding in the case of bone cements, tissue necrosis, a well known problem of acrylic bone cements.

The hardenable compositions formed from the invention also display a long working time thereby providing a longer time period for the operator to manipulate the cement dough in the desired fashion during application.

Advantageously, when water is the liquid carrier for the acrylic polymer particles, the final cured hardened cement composition is porous. This porosity allows the mechanical properties of the hardenable composition to be matched to those of e.g. vertebral bone, thereby avoiding well known problems associated through implantation of artificial materials that are higher in modulus than the surrounding natural bone. However, the formulation can be also altered to adjust the level of porosity and vary the mechanical properties, e.g., to achieve mechanical properties that satisfy the requirements of ISO 5833:2002.

In addition, as a result of the porosity, the polymerization shrinkage upon setting of compositions of the invention may be lower than would normally be expected of conventional hardenable compositions based on powder/liquid combinations.

A still further advantage of the invention when used as a bone cement is that the control of porosity (size and topography) allows improved control over the controlled release of antibiotics and other medicines into the surrounding bone and tissue.

The polymerization of at least one acrylic monomer composition to produce an acrylic polymer particle may take place with or without excess initiator.

Typically, a preferred embodiment of the hardenable composition of the invention is prepared by:— dispersing the radiopacifying filler in acrylic monomer/polymer syrup to produce a dispersion; suspension polymerising the dispersion to produce acrylic polymer bead particles containing encapsulated and/or adsorbed filler;

mixing the acrylic polymer bead particles containing encapsulated and/or adsorbed filler with an acrylic polymer emulsion to form the liquid first part;

producing a liquid second part containing acrylic monomer and accelerator;

mixing the liquid first part with the liquid second part to make a dough;

optionally, placing the dough in a mould or cavity by hand manipulation or injection; and allowing the dough to set and harden.

The initiator may be present in the liquid first part as excess initiator from either the emulsion or dispersion polymerization or may be separately added to the dispersion, emulsion or first part prior to mixing with the second part.

In a preferred embodiment, a two part composition comprises a first liquid part which typically comprises polymer beads (usually with mean particle size of about 10-200 μm) of typically, poly(methyl methacrylate) (PMMA), the encapsulated and/or adsorbed radiopacifying filler and a small amount of polymerisation initiator such as dibenzoyl peroxide (BPO), usually also encapsulated within the PMMA bead, but which can also be added as a separate component. The second liquid part is usually a monomer, typically methyl methacrylate (MMA), which may also contain a polymerisation activator such as N, N-dimethyl-p-toluidine (a tertiary amine) (DMPT) and an inhibitor such as hydroquinone (HQ) to prevent the monomer from spontaneously polymerising.

When the two liquid parts are mixed together, the acrylic polymer particles are wetted with monomer, solvated and begin to dissolve. If present, the lower average particle size particles dissolve at a faster rate. The solvated polymer particles release dibenzoyl peroxide initiator into the monomer which interacts with activator, if present, to produce radicals that react with the monomer and initiate room temperature addition polymerisation of the monomer. The mixture starts out as a relatively low viscosity cement and progresses to a stiffer and stiffer system that eventually hardens completely to its final set composition.

This constantly changing viscosity of the cement is characterised by dough and set times and maximum exotherm temperature attained, as defined by BS ISO 5833:2002. The dough time is considered to be the length of time following the start of mixing for the cement to achieve a dough-like mass that does not adhere to a gloved finger when gently touched. The set time is considered to be the time taken to reach a temperature midway between ambient and maximum.

The dough and set times and maximum exotherm temperatures are very important parameters that determine how the hardenable compositions are to be used. Compositions hardenable at room temperature (so-called "self-curing" or "cold-curing" systems) have dough times that are typically 4 to 10 minutes and set times that are typically 10 to 25 minutes in duration. These parameters effectively define the time period available for the operator to manipulate the dough in the desired fashion, for example pressing into a denture mould for denture base manufacture, or pressing into a bone cavity during hip repair or replacement or injecting into a vertebral cavity during spinal surgery. It may be advantageous to maximise the working time available to the operator. This should ideally be achieved without an increase in the set time as this defines the end point for the cementing or fixing operation. This therefore focuses attention on shortening the dough time. The dough time is determined by the rate at which the combination of liquid components rises in viscosity immediately after mixing and is controlled by a number of factors, such as polymer bead particle size and shape, polymer molecular weight, and polymer composition.

Polymer Beads

Preferably, as mentioned above, the acrylic polymer particles comprise polymer beads. Such beads are preferably not formed of emulsion polymerized particles but are preferably produced by conventional non-emulsion polymer processing. Such polymer beads are well known to the skilled person in the field of acrylic polymer compositions and may, for example, be those made by bulk, solution or suspension polymerization. Typically, the beads are made by suspension polymerization. Mixing of the beads with a liquid carrier such as that provided by an acrylic polymer emulsion or water forms a dispersion of the polymer beads in the liquid carrier. Typically, this is a dispersion of the bead polymer in a continuous emulsion phase.

The term beads as used herein is not meant to be interpreted restrictively unless indicated otherwise and refers to a discrete polymer particle of any suitable size, shape and surface texture. In the context of the present application however, the term bead may be used to differentiate this type of acrylic polymer particle from emulsion particles.

Polymer and Other Component Amounts

Typically, the acrylic polymer particles of the invention form at least 98% w/w of the undissolved polymer present in the composition prior to mixing, more preferably, at least 99% w/w, most preferably, approximately 100% w/w of the undissolved polymer present in the composition prior to mixing. Upon mixing the monomer polymerizes and causes the mixed composition to form a cement which gradually hardens eventually setting to a solid. Some polymer, preferably, acrylic polymer as defined herein may also be dissolved in the monomer composition prior to mixing. Such levels of dissolved polymer are typically in the range 0-60% w/w in the acrylic monomer component, more typically 10-30% w/w.

Typically, the solids content of a liquid part of the multi-part composition which comprises the acrylic polymer particles and encapsulated and/or adsorbed radiopacifying filler may be in the range 10-95% w/w, more typically, 20-92% w/w, most typically, 30-90% w/w. The preferred ranges depend on the properties that are desired, e.g. mechanical properties. For example, to achieve a compressive strength in the resulting solid of greater than 40 MPa, the preferred range of solids content of the liquid part is 60-95% w/w, more preferably, 65-95% w/w, most preferably, 70-90% w/w.

The acrylic polymer particles together with encapsulated and/or adsorbed radiopacifying filler may typically form between 50-99.9% w/w of the solids content of a liquid part of the multi-part composition which comprises the acrylic polymer particles and encapsulated and/or adsorbed radiopacifying filler, more preferably, 60-97.5% w/w, most preferably, 65-94.5% w/w. The balance in such a liquid part is generally made up of other solids which may be fillers, pigments, dyestuffs, catalysts, non-encapsulated radiopacifying filler and initiator, although residual emulsifier may also be present.

If both present, the ratio of emulsion polymerised acrylic polymer particles to non-emulsion polymerized acrylic polymer particles such as beads varies depending on the final application. Nevertheless, it is advantageous in some applications such as bone cements to have a ratio thereof of between 2:98 to 50:50 w/w thereof, more preferably, 3:97 to 40:60 w/w, most preferably, 5:95 to 30:70 w/w. Such a ratio gives a good balance between short dough times and long work times. However, no restriction should be taken hereby and other emulsion polymerized particle ratios are also possible such as 0% or 100% w/w emulsion polymerized particles forming the acrylic polymer particle component or a ratio of 30:70 to 70:30, more typically, 40:60 to 60:40. As indicated, it is also possible for the acrylic polymer particles to be formed of up to 100% bead polymer particles i.e. 0% emulsion polymer particles.

The liquid carrier is sufficient to act as a liquid carrier for the solid components whether emulsified or otherwise suspended therein. The liquid carrier may thus form between 5-90% w/w of the liquid part in which acrylic polymer particle encapsulated and/or adsorbed radiopacifying filler is found, more typically, 8-80% w/w, most typically, 10-70% w/w.

The other liquid part may include monomer, water or other solvent as the liquid component which is sufficient to provide a liquid carrier for the other components which may include other polymer composition components known to the skilled to the skilled person such as polymer, initiator (if monomer is absent), fillers, pigments, dyestuffs, catalysts, accelerators, plasticisers etc. In this regard, although it is possible to use an initiator paste in a liquid carrier such as water or organic solvent, optionally in the presence of plasticizer to form a liquid part of the composition, it is more typical to have acrylic monomer as a liquid carrier in one part, optionally with acrylic polymer particles dissolved therein and with other components added such as accelerators, fillers, dyes etc. Generally, the amount of monomer in the hardenable composition, whether in the first part, second, third or further part, is in the range 10-70% w/w, more typically 15-60% w/w, more preferably 20-50% w/w.

When both monomer and acrylic polymer dissolved resin or particles form the bulk of a liquid part, the ratio of acrylic monomer:polymer is in the range 99:1 to 40:60 w/w.

The ratio of the liquid first part to the liquid second part is preferably in the range 2:1 to 1:20 by mass, more preferably, 1:1 to 1:2 by mass, this is particularly applicable to the arrangement of the encapsulated and or adsorbed radiopacifying filler being substantially located in the liquid first part and the acrylic monomer component being substantially located in the liquid second part.

Typically, the level of filler in the hardenable acrylic composition of the invention whether radiopacifying or otherwise is 1-55% w/w of the acrylic composition, more preferably, 5-45% w/w, most preferably, 6.5-35% w/w. The filler may be present in any one of the liquid parts or may be distributed in two or more parts.

Preferably, at least 90% w/w of the total radiopacifying filler in the composition is present in the liquid first part, more preferably, at least 95% w/w, most preferably, at least 99% w/w and in any case, preferably in suspension therein. In preferred embodiments, substantially all the radiopacifying filler in the composition is present in the liquid first part, preferably in suspension therein. Typically, therefore, the radiopacifying filler is present in only one part of the composition.

Typically, all or substantially all of the said acrylic monomer component and the said radiopacifying filler are located in separate parts of the composition so that the radiopacifying filler is not substantially present in the polymer matrix of the final hardened material.

Preferably, at least 90% w/w of the total acrylic polymer particles with encapsulated and/or adsorbed radiopacifying filler in the composition are present in the liquid first part, more preferably, at least 95% w/w, most preferably, at least 99% w/w and in any case, preferably in suspension therein. In preferred embodiments, substantially all the acrylic polymer particles with encapsulated and/or adsorbed radiopacifying filler in the composition is present in the liquid first part, preferably in suspension therein. Typically, therefore, the acrylic polymer particles with encapsulated and/or adsorbed radiopacifying filler are present in only one part of the composition prior to mixing.

Typically, all or substantially all of the said acrylic monomer component and the said acrylic polymer particles with encapsulated and/or adsorbed radiopacifying filler are located in separate parts of the said composition so that encapsulated and or adsorbed radiopacifying filler is not released into the monomer component prior to mixing and therefore released radiopacifying filler presence in the polymer matrix of the final hardened material is reduced.

Preferably, at least 90% w/w of the total emulsion polymerized acrylic particles present in the composition is present in the liquid first part, more preferably, at least 95% w/w, most preferably, at least 99% w/w. In preferred embodiments, substantially all the emulsion polymerized acrylic particles in the composition is present in the liquid first part. Typically, therefore, the emulsion polymerized acrylic particles are present in only one part of the composition.

Typically, all or substantially all of the said acrylic monomer component and the said emulsion polymerized acrylic particles, if the latter is present, are located in separate parts of the said composition so that, for example, the liquid carrier of the first part is provided by the emulsion liquid carrier and a liquid carrier for the second part is provided by the acrylic monomer.

Accelerators may be present in the unmixed composition in the range 0.1 to 5% by mass, more typically, 0.5-3% by mass.

The total level of unreacted initiator, whether residual or added, in the multi-part acrylic composition is typically, 0.1-10% w/w of the acrylic composition, preferably, 0.15-5% w/w, more preferably, 0.2-4.0% w/w.

Where initiator is used in one of the components, this may itself be encapsulated within the polymer bead and/or polymer emulsion or separately added to any of the liquid parts. Although it is possible to have initiator in the liquid part with the acrylic monomer component such would only have a short shelf life. Accordingly, typically, the initiator and acrylic monomer component are located in separate parts of the composition.

Where polymer is dissolved in monomer in any of the liquid parts, the polymer must contain very low (e.g. <0.1% w/w) levels of residual initiator to avoid shortening of the shelf life.

The initiator may be present in acrylic polymer particles that form part of the acrylic polymer composition. The initiator in the acrylic polymer particles may be the residual amount of unreacted initiator used in the formation of the particles which is therefore the equivalent of the excess amount of initiator. Some initiator can alternatively or additionally be added as a separate component to the multi-part composition. In the polymerized acrylic particles, the level of residual initiator present before reaction is typically, 0.001-10% w/w of the emulsion polymerized acrylic particles, preferably, 0.1-6% w/w, more preferably 0.1-5% w/w.

Preferably, the initiator is present at a level which will effect polymerization of the monomer component that is at least greater than 90% polymerization, more typically, greater than 93%, more typically greater than 95% polymerization.

If more than one sub-population of acrylic polymer particles is present in the composition they may be present in the same liquid part and/or in different liquid parts. In a preferred embodiment, a first sub-population with encapsulated and/or adsorbed radiopacifying filler is present in the first liquid part with optionally, one or more further sub-populations of acrylic polymer particles which may or may not have encapsulated and/or adsorbed radiopacifying filler and a second sub-population with optionally further sub-populations, is present in the liquid second part dissolved or partly dissolved in the acrylic monomer component. A preferred further sub-population in the liquid first part is emulsion polymerised particles and a preferred liquid carrier is the liquid carrier for the emulsion of emulsion polymerized particles, typically, water.

The acrylic polymer particles with encapsulated and/or adsorbed radiopacifying filler may be mixed with an emulsion of emulsion polymerized particles to form a suspension in the water emulsion phase. In any case, the polymer components are typically, in the presence of suitable other polymer composition components known to the skilled person. Such polymer composition additives include initiators, emulsifiers, catalysts, pigments, dyestuffs and fillers.

Specific Materials

Initiators that can be used to initiate the emulsion polymerization and therefore those which may form residual initiators in the composition to initiate the hardening process are persulphates, (e.g., potassium, sodium or ammonium), peroxides (e.g., hydrogen peroxide, dibenzoyl peroxide, tert-butylhydroperoxide, tert-amylhydroperoxide, di-(2-ethylhexylperoxydicarbonate or lauroyl peroxide) and azo initiators (e.g., 4,4'-azobis(4-cyanovaleric acid)).

In addition to the emulsion initiators above, a particularly preferred initiator for the hardening stage is dibenzoyl peroxide.

Initiators that can be used for conventional or emulsifier free emulsion polymerization and therefore which may be present as residual initiators include:—ionic water-soluble initiators, such as potassium, sodium or ammonium persulphate.

In addition, any one or more of the above initiators can be added to the composition independently.

In a particularly preferred embodiment, the emulsion or bead particles incorporate the initiator in their polymer matrix. Accordingly, in this embodiment, the initiator is not added separately to the liquid first part of the composition.

Advantageously, the initiator for the hardenable composition can be added as excess initiator during the polymerization of the particles so that some initiator is used in the polymerization of the particles but as the particles form, the excess initiator is incorporated into the polymer matrix. Subsequently, after wetting and dissolution with monomer, the initiator is released and thus able to initiate the hardening phase. In a core/shell particle, the initiator is preferably incorporated in the outer shell i.e. during the final stage of the multistage emulsion polymerization process and, accordingly, excess initiator is used in the final shell polymerization stage. During polymerization of the polymer particle more than one initiator may also be used. In the case of multiple initiators, it is advantageous for one of the initiators to be substantially used up in the polymerization and a second initiator to be in excess and only partly used so that the excess amount of the second initiator is incorporated into the particles. This procedure may be assisted by the initiators having different half lives so that a shorter half life initiator (i.e., an initiator with a higher decomposition rate at a given temperature and reaction medium) is used up preferentially. In addition, a higher temperature can be used to drive the polymerization to completion in the presence of the first initiator whilst a lower temperature can retard polymerization of monomer in the presence of the second initiator intended as a residual initiator. However, some of the second initiator will inevitably be used up because to incorporate the initiator into the particle some polymerization must take place in the presence of the second initiator. Whether one or more initiators are used, the amount of initiator left as residue depends on the time of exposure of the initiator to polymerization conditions and reactants, and the relative reactivity to the first initiator, if present. It will be appreciated by the skilled person that the exact amount of residual initiator will be dependent on the experimental conditions and can easily be determined by trial and error and then be made reproducible by careful control of quantities of monomers and initiators and process conditions. The time of addition of the initiator in excess is also relevant to the molecular weight of the polymer. If added too early in the polymerization, the molecular weight of the particle will be reduced. Accordingly, the molecular weight required will also influence the time of addition of the initiator in excess so that the excess initiator is incorporated whilst achieving the molecular weight required for the particular application.

Preferably, step (a) of the method of production of the invention when including emulsion particles comprises seed, core and at least one shell emulsion polymerization step. A particularly preferred method introduces an excess of initiator into the emulsion polymerization step so that residual initiator is encapsulated within the emulsion particles. Preferably, in a multistage emulsion polymerization, the excess initiator is introduced during the final stage so that it is present in the outer shell of the multistage particle. However, alternatively, initiator can also be added subsequently to the acrylic polymer emulsion.

For the avoidance of doubt, by "excess initiator" is meant, the portion of initiator that is not required to complete polymerisation of the acrylic polymer particles and is available for subsequent reaction after the initial polymerization of the acrylic polymer particles is terminated.

Variation in the amount of encapsulated residual initiator or added initiator (e.g. dibenzoyl peroxide) has the effect of varying the set time of the hardenable composition. Increased initiator level results in shortened set time. Additionally, variation of the amount of accelerator (e.g. DMPT) in the acrylic monomer composition can also affect the set time. Increased accelerator concentration results in shortened set time.

Typically, herein, initiator will be present in the composition at a level of 0.1 to 5% w/w total monomer and initiator.

In compositions according to the invention other fillers may be used and these will be known to the skilled person in the art of such fields. Additionally, organic x-ray opaque monomers can be used in addition to fillers. These can be copolymerized into any of the acrylic polymer particles during their production or incorporated into the acrylic monomer composition. Typical organic x-ray opaque monomers include halogenated methacrylates or acrylates, e.g., 2,3-dibromopropyl methacrylate or 2-methacryloyloxy-ethyl-2,3,5-triiodobenzoate. For the avoidance of any doubt, such x-ray opaque monomers are not to be regarded as fillers or radiopacifying fillers.

Emulsifiers that can be used in the emulsion polymerization and therefore those which are present in the subsequent liquid part where the emulsion provides the liquid carrier are those that are typical in conventional emulsion polymerization, including anionic (e.g., sodium dioctyl sulfosuccinate, disodium ethoxylated alcohol half ester of sulfosuccinic acid, tetrasodium N-(1,2-dicarboxy ethyl)-N-octadecyl sulfosuccinate, sodium salt of sulphated alkylphenol ethoxylates, sodium alkane sulfonate, sodium dodecyl sulphate or sodium 2-ethylhexyl sulphate), nonionic (e.g., polyethylene glycol nonylphenyl ethers, polyethylene oxide octylphenyl ethers, or di-functional ethylene oxide/propylene oxide block copolymers) or cationic emulsifiers (e.g., hexadecyl-trimethylammonium bromide or alkyl polyglycoletherammonium methyl chloride). Reactive or polymerisable emulsifiers or surfactants suitable for use with acrylic emulsions can also be used, e.g., sodium dodecylallyl sulfosuccinate, styrene sodium dodecylsulfonate ether, dodecyl sodium ethylsulfonate methacrylamide, methacrylic or vinylbenzyl macromonomers of polyethylene oxide or ethylene oxide/propylene oxide block copolymers or methacryloylethyl-hexadecyldimethylammonium bromide.

The mixing of the further components of the invention with the liquid carrier in any of the liquid parts may be carried out by any suitable technique known to the skilled person for mixing solids or liquids with a liquid.

Preferably, the Z-average particle size of the emulsion polymerized acrylic polymer particles is less than 2000 nm as determined by light scattering using a Malvern Zetasizer nano series S particle size analyzer (adding one drop of emulsion to 1 ml of de-ionised water in a measurement cuvette, allowing the test sample to equilibrate at 25° C. and determining Z-average particle size using the software provided by the instrument), more preferably, less than 1000 nm, most preferably, less than 800 nm, especially, less than 700 nm. A preferred Z-average particle size range for the emulsion polymerized particles is between 10-2000 nm, more preferably, 50-1000 nm, most preferably, 100-800 nm, especially 150-600 nm, as determined by light scattering using a Malvern Zetasizer as above.

The core shell (C:S) ratio of the emulsion polymerised acrylic particles is typically, between C:S 95:5% wt and C:S 40:60% wt, more typically, between C:S 90:10% wt and C:S 50:50% wt, preferably, between C:S 85:15% wt and C:S 70:30% wt.

Typically, the emulsion polymerized acrylic polymer particles may be single stage or multistage i.e. the so called core/shell particles. In this regard, it may be adequate to use a single monomer such as methyl methacrylate for making seed, core and shell. In this case, particularly if the composition and molecular weight of the seed, core and shell are designed to be the same, standard single stage emulsion polymerization techniques known to the skilled person could be deployed. However, to obtain emulsion particles that display some control over their structure, particularly their composition, particle size and molecular weight, it is preferable to use the multistage core-shell emulsion polymerization approach.

For manufacturing core-shell particles by emulsion polymerization, it is convenient to employ the widely used method of initially forming seed particles, which then act as nuclei for further growth, i.e. to produce a polymeric core and then shell. The concept is described in more detail by V. L. Dimonie, et al, "Emulsion Polymerization and Emulsion Polymers", P. A. Lovell and M. S. El-Aasser, Eds, John Wiley & Sons Ltd, Chapter 9, pages 294-326, (1997). The seed particles may be formed and stabilised using either emulsifier-free techniques (i.e., particle stabilisation arising from the use of ionic water-soluble initiators, such as potassium, sodium or ammonium persulphate) or through using emulsifiers. Once the seed particles are formed, the core and shell are formed from sequential addition of further aliquots of monomer and initiator.

The Brookfield viscosity range for the liquid parts of the invention may independently be between 0.01 and 10 Pascal second (Pa.$), more preferably between 0.5 to 7 Pa·s, still more preferably between 0.8 to 5 Pa·s, most preferably between 1 to 4 Pa·s.

A particular problem in the case where one liquid part is comprised of acrylic polymer particles in a dispersion or emulsion is that the viscosity of the liquid part can be relatively high in comparison to a further liquid part composed of an acrylic polymer dissolved in acrylic monomer, particularly when the further liquid part is a relatively low viscosity syrup. As mentioned above, it can be problematic if the viscosity of one or both of the liquids is too high or the viscosity of the two or more liquids are significantly different to each other. To facilitate better mixing, the Brookfield viscosity of each liquid part may independently be between 0.3 and 10 Pa·s, more preferably between 1 and 4 Pa·s, most preferably between 1 and 2 Pa·s and it is especially preferred if all parts fall within these specified increasingly preferred ranges. In the present invention, it is therefore advantageous to control the viscosity of such high viscosity liquid parts so that the high viscosity is lowered to a level that provides a suitable viscosity for delivery of the multi-part bone cement from separate respective containers of a device having two or more containers, such as a twin barrelled syringe, to the outlet thereof. Typically, such devices also require a mixer to mix the extrudate of the multiple containers together before the outlet, such as a static mixer. The increasing viscosity of the hardening composition as it travels through the mixer towards the outlet of the device can be influenced by the viscosity of the liquid parts. Controlling the viscosity of the liquid part containing acrylic polymer particles with encapsulated and/or adsorbed radiopacifying filler may be achieved by adapting the components of the part by:

(i) providing, in the part, a sub-population of acrylic polymer particles with a different average particle size to the acrylic polymer particles with encapsulated and/or adsorbed radiopacifying filler; and optionally (ii) providing at least one further sub-population(s) of acrylic polymer particles in the part having different respective average particle sizes from the other sub-populations.

Advantageously, at least the sub-population in part (i) has a lower average particle size than the sub-population of acrylic polymer particles with encapsulated and/or adsorbed radiopacifying filler. The sub-populations may independently be bead or emulsion particles as defined herein.

Accordingly, to provide advantageous viscosities for liquid compositions of the present invention the Z-average particle size of any emulsion polymerized acrylic polymer particles or any sub-populations thereof may independently be greater than 100 nm, more preferably greater than 200 nm, for instance, in the range 100-900 nm, most preferably 200-800 nm. Furthermore, the mean particle size of any bead type acrylic polymer particles may be 1-1,000 µm, preferably 15-600 µm, more preferably 15-400 µm, most preferably 20-300 µm.

Preferably, therefore the liquid part containing acrylic polymer particles with encapsulated and/or adsorbed radiopacifying filler comprises in the liquid part a first sub-population of emulsion polymerized acrylic polymer particles and a second or further sub-population/s of emulsion polymerised acrylic polymer particles having different Z-average particle size/s from the first emulsion polymerised acrylic polymer particles.

Preferably, therefore, the liquid part containing acrylic polymer particles with encapsulated and/or adsorbed radiopacifying filler comprises in the liquid part two or more sub-populations of acrylic polymer particle having different respective average particle sizes from each other. However, as mentioned above, at least one has a lower average particle size than the sub-population of acrylic polymer particles with encapsulated and/or adsorbed radiopacifying filler. Preferably, where there are two or more sub-population/s of acrylic polymer particles there is at least 1 wt % of each sub-population, more preferably, 5 wt %, most preferably, 10 wt %. For example, where there are two sub-populations the typical ratios are in the range 1-99:99-1 wt %, more typically, 10-90:90-10 wt %. For further example, where there are three types, the typical ratios are in the range 1-98:98-1:98-1 wt %, more typically, 5-90:90-5:90-5 wt %.

Preferably, the compressive strength of the solid produced by mixing the said liquid parts in any aspect of the present invention is greater than 40 MPa, more preferably greater than 50 MPa. The typical range of compressive strengths found in the produced solid is 40-80 MPa, more preferably 50-80 MPa.

Definitions

The term "adsorbed" takes its usual meaning and means bound to the surface thereof.

The term "liquid" herein does not require definition because it is well understood by the skilled person. However, for the avoidance of doubt it also includes a flowable material having a liquid carrier such as a slurry, suspension, emulsion paste that is thus susceptible of delivery through a syringe or caulking gun outlet by the application of pressure. Typically, the term liquid is applicable to the material or composition at least between 5 and 35° C., more typically, between 5 and 30° C.

By "storage stable" is meant that the monomer or liquid does not polymerize under normally acceptable storage conditions of temperature and time i.e. between 5 and 30° C. and 1 to 250 days, more typically, 15 to 25° C. and 1 to 170 days.

The term "sub-population" is generally understood by the skilled person but for the avoidance of doubt refers to a plurality of polymer particles having a specific molecular weight (MW), molecular weight distribution, porosity, nature and distribution of (co)monomer residues, average particle size, particle size distribution, the presence or absence of residual initiator and, if present, the amount and type of residual initiator and/or type as is usually produced by monomer(s) which have undergone the same polymerization process(es) together.

The term "lower" herein in the context of average particle size or the like means having a lower value but is preferably, at least 10% lower than the comparative larger value, more preferably, at least 20% lower, most preferably at least 50% lower than the larger value.

The Z-average particle size herein is determined by light scattering using a Malvern Zetasizer nano series S particle size analyzer.

The mean particle size herein may be determined using a Coulter LS230 laser diffraction instrument.

The method of manufacture of acrylic bead polymer particles is generally conventional suspension or dispersion polymerization to produce generally spherical polymer particles, or beads. However, other methods of manufacture are also possible, e.g., bulk polymerization or solution polymerization followed by evaporation of the solvent.

By acrylic polymer herein whether in relation to the acrylic polymer particles or otherwise is meant independently for each sub-population a homopolymer of a polyalkyl(alk)acrylate or (alk)acrylic acid or copolymers of a alkyl(alk)acrylate or (alk)acrylic acid with one or more other vinyl monomers. Typically, a homopolymer of methyl methacrylate or a copolymer of methyl methacrylate with one or more other vinyl monomers is used. By other vinyl monomers is included a further alkyl(alk)acrylate or (alk)acrylic acid such as ethyl methacrylate, methyl acrylate, ethyl acrylate, n-butyl acrylate, iso-butyl acrylate, t-butyl acrylate, n-butyl methacrylate, iso-butyl methacrylate, t-butyl methacrylate, 2-ethylhexy methacrylate, 2-ethylhexyl acrylate, lauryl methacrylate, lauryl acrylate, cyclohexyl acrylate, cyclohexyl methacrylate, isobornyl acrylate, isobornyl methacrylate, methacrylic acid or acrylic acid; hydroxyl-functional acrylates such as 2-hydroxyethyl methacrylate, hydroxypropylethyl methacrylate, 2-hydroxyethyl acrylate, or hydroxypropyl acrylate; vinyl compounds such as styrene, vinyl pyrrolidinone or vinyl pyridine; and compatible crosslinking monomers such as allyl methacrylate, divinyl benzene, ethylene glycol dimethacrylate, ethylene glycol diacrylate, 1,4-butanediol dimethacrylate, 1,4-butanediol diacrylate, 1,6-hexanediol dimethacrylate or 1,6-hexanediol diacrylate, particularly the compatible acrylic crosslinking monomers.

Copolymers containing functionalized monomers are of special interest because they may help in dispersing non-encapsulated radiopacifying fillers into the monomer containing part. Suitable functionalized monomers are well known in the field of pigment dispersion in inks and coatings. For example, amines such as N,N-dimethylaminoethyl methacrylate, N,N-diethylaminoethyl methacrylate, t-butylaminoethyl methacrylate and acids such as methacrylic acid and acrylic acid.

Crosslinking monomers can be used to crosslink the acrylic polymer particles or one or more of the acrylic polymer particle sub-populations. For the emulsion polymerized particles, crosslinking may be carried out in the core and the shell, or only the core, or only the shell. Crosslinking serves the purpose of fine-tuning the properties of the hardenable multi-part acrylic composition.

The weight average molecular weight (Mw) of the emulsion polymerized acrylic polymer particles is typically, between 25,000 daltons and 3,000,000 daltons, more typically, between 100,000 daltons and 1,500,000 daltons, preferably, between 250,000 and 1,000,000, for instance, between 250,000 and 600,000. Molecular weight may be determined for this purpose by gel permeation chromatography (GPC).

Although, the molecular weights of the polymers in the polymer components of the hardenable composition may influence the dough and work times, the invention is not restricted to any particular molecular weight. In any case, reductions in the molecular weight and/or increases in the particle size of the acrylic polymer particles can be used to increase the work time of the hardenable composition.

The weight average molecular weight (Mw) of the bead type of polymer particles, if present, is typically, between 10,000 daltons and 3,000,000 daltons, more typically, between 30,000 daltons and 1,000,000 daltons, preferably, between 50,000 and 700,000, for instance, between 60,000 and 600,000 Daltons. Molecular weight may be determined for this purpose by gel permeation chromatography (GPC).

By acrylic monomer herein is meant any one or more suitable alkyl(alk)acrylate or (alk)acrylic acid such as methyl methacrylate, ethyl methacrylate, methyl acrylate, ethyl acrylate, methacrylic acid or acrylic acid, n-butyl acrylate, iso-butyl acrylate, t-butyl acrylate, n-butyl methacrylate, iso-butyl methacrylate, t-butyl methacrylate, 2-ethylhexy methacrylate, 2-ethylhexyl acrylate, lauryl methacrylate, lauryl acrylate, cyclohexyl acrylate, cyclohexyl methacrylate, isobornyl acrylate or isobornyl methacrylate; hydroxyl-functional acrylates such as 2-hydroxyethyl methacrylate, hydroxypropylethyl methacrylate,2-hydroxyethyl acrylate, or hydroxypropyl acrylate; vinyl compounds such as styrene, vinyl pyrrolidinone or vinyl pyridine; and compatible crosslinking monomers such as allyl methacrylate, divinyl benzene, ethylene glycol dimethacrylate, ethylene glycol diacrylate, 1,4-butanediol dimethacrylate, 1,4-butanediol diacrylate, 1,6-hexanediol dimethacrylate or 1,6-hexanediol diacrylate, particularly the compatible acrylic crosslinking monomers. Alternatively, the suitable acrylic monomers may exclude ethyl methacrylate and/or n-butyl methacrylate from the foregoing. Typically, methyl methacrylate is the monomer component of the invention.

The acrylic monomer component of the invention is optionally, provided with an accompanying suitable inhibitor such as hydroquinone (HQ), methyl hydroquinone (MeHQ), 2,6-di-tertiary-butyl-4-methoxyphenol (Topanol O) and 2,4-dimethyl-6-tertiary-butyl phenol (Topanol A). The inhibitor is present to prevent the monomer from spontaneously polymerising. A suitable inhibitor is 60 ppm of hydroquinone to ensure long shelf life at room temperature.

Polymerization activators or accelerators may also be optionally present, such as N,N-dimethyl-p-toluidine (DMPT) and N,N-dihydroxyethyl-p-toluidine (DHEPT) (both tertiary amines) or organic-soluble transition metal catalysts. The presence of activators or accelerators depends upon the final application. Where "cold-cure" is necessary such as in dental or bone cement applications, an accelerator is usually necessary. However, for some applications the use of heat in "heat-cure" systems is also possible. For instance, dentures can be activated by heat. When present in the composition, accelerator is typically present at a level that will effectively activate the polymerisation reaction in the presence of initiator, typically, this is at a level of 0.1 to 5% w/w total monomer and accelerator.

By alkyl herein is meant $C_1$-$C_{18}$ alkyl wherein the term alkyl and alk encompasses cycloalkyl and hydroxyl functional $C_1$-$C_{18}$ alkyl. By alk herein is meant $C_0$-$C_8$ alk.

In one preferred embodiment, the acrylic polymer composition liquid part containing the acrylic polymer particles having encapsulated and/or adsorbed radiopacifying filler comprises an emulsion of polymerized acrylic polymer particles and only a single sub-population of acrylic polymer bead particle, the former generally to control the dough time and the latter to generally control the working time.

By "acrylic composition" is meant a composition where at least 50% of the total monomer and monomer residues present are present as or derived from one or more of the above defined acrylic monomers, more typically, is meant at least 70%, most typically, 95% or especially, 99% of the total monomer or monomer residues present.

In a preferred two-part embodiment of the invention the first liquid part comprises emulsion polymerized acrylic polymer particles in, preferably suspended in, a liquid carrier (preferably, PMMA emulsion), a sub-population of acrylic polymer bead particle with encapsulated and/or adsorbed radiopacifying filler (preferably PMMA bead) and initiator and the second part comprises acrylic monomer (preferably MMA monomer) and accelerator. Optionally, in this embodiment the Z-average particle size of the emulsion polymerized acrylic polymer particles is lower than the acrylic polymer bead mean particle size with encapsulated and/or adsorbed radiopacifying filler In a further preferred two-part embodiment of the invention the first part comprises emulsion polymerized acrylic polymer particles in, preferably suspended in, a liquid carrier (preferably PMMA emulsion), a sub-population of acrylic polymer bead particle with encapsulated and/or adsorbed radiopacifying filler and initiator and the second part comprises a solution of initiator-free acrylic polymer (preferably PMMA), in acrylic monomer (preferably MMA) with accelerator. Optionally, in this embodiment the Z-average particle size of the emulsion polymerized acrylic polymer particles is lower than the acrylic polymer bead mean particle size with encapsulated and/or adsorbed radiopacifying filler.

In a further preferred two-part embodiment of the invention the first part comprises a first sub-population of acrylic polymer bead particles in, preferably suspended in, a liquid carrier (preferably water), a sub-population of acrylic polymer bead particle with encapsulated and/or adsorbed radiopacifying filler and initiator (optionally, encapsulated in one or both bead populations) and the second part comprises a solution of initiator-free acrylic polymer (preferably PMMA), in acrylic monomer (preferably MMA) with accelerator. Optionally, in this embodiment the mean particle size of the acrylic polymer bead particles is lower than the acrylic polymer bead mean particle size with encapsulated and/or adsorbed radiopacifying filler.

In a further preferred embodiment of the invention the first part comprises acrylic polymer bead particles with encapsulated and/or adsorbed radiopacifying filler (preferably PMMA bead) and initiator in, preferably suspended in, a liquid carrier and the second part comprises acrylic monomer (preferably, MMA monomer) and accelerator.

In a further preferred embodiment of the invention the first part comprises acrylic polymer bead particles with encapsulated and/or adsorbed radiopacifying filler (preferably PMMA bead) in, preferably suspended in, a liquid carrier, and initiator and the second part comprises a solution of initiator-free acrylic polymer bead (preferably PMMA bead) in acrylic monomer (preferably, MMA monomer) and accelerator.

In a further preferred embodiment of the invention the first part comprises a initiator-free acrylic polymer bead with encapsulated and/or adsorbed radiopacifying filler (preferably PMMA bead), emulsion polymerized acrylic polymer particles in, preferably suspended in a liquid carrier, acrylic monomer (preferably, MMA monomer) and accelerator and the second part comprises an initiator paste. Initiator pastes are available commercially usually as a mixture with water or plasticiser. Optionally, in this embodiment the Z-average particle size of the emulsion polymerized acrylic polymer particles is lower than the mean particle size of the acrylic polymer bead particle with encapsulated and/or adsorbed radiopacifying filler.

Advantageously, in the present invention the monomer and initiator are kept in separate parts of the multi-part composition so that monomer is added from one part when unreacted initiator is present in another part and so that initiator is added from the other part when no unreacted initiator but instead monomer is present in the one part.

Notwithstanding the foregoing, a particularly advantageous application of the acrylic composition of the aspects of the invention is its use as bone cement compositions. Such compositions are used in vertebroplasty. A similar application for the compositions of the present invention is dental repairs.

Emulsion polymerized particles are well known in the field of impact modifiers. For this reason an impact modifier such as butadiene or butyl acrylate is typically introduced as a comonomer into one of the shells of the multistage core shell particle. However, in the multi-part compositions of the present invention, an impact modifier may not be required. Accordingly, the emulsion polymerized acrylic polymer particles of the present invention may be free from impact modifier co-monomer residues.

The acrylic composition liquid part of the present invention containing the encapsulated and/or adsorbed radiopacifying filler may be provided separately as a liquid either with or without added further components as defined herein for later use as a liquid part in a hardenable composition.

Accordingly, according to a further aspect of the present invention there is provided a liquid composition comprising a first sub-population of emulsion or non-emulsion polymerized acrylic polymer particles, and optionally at least one further sub-population of emulsion or non-emulsion polymerized acrylic polymer particles and characterized in that there is a polymerization initiator in the liquid composition at a level sufficient to cause the liquid composition to harden upon contact with a reactive monomer liquid and in that radiopacifying filler is encapsulated and/or adsorbed in the first sub-population of acrylic polymer particles. Preferably, the acrylic polymer particle sub-populations are suspended in a liquid part of the composition. Typically, one or more of the further sub-population(s) of acrylic polymer particles in the composition have a lower average particle size than the average particle size of the first sub-population having encapsulated and/or adsorbed radiopacifying filler.

There is no particular temperature limitation on the use of the present invention. Generally, however, it is used at temperatures acceptable to the operator i.e. temperatures found during normal working conditions that may be encountered indoors or outdoors by the operator, for example 5-40° C. and atmospheric pressure and/or applied syringe pressure . . . .

Therefore, according to a further aspect of the present invention there is provided a syringe or caulking gun having at least two barrels comprising the liquid first part according to the present invention in a first barrel thereof and a liquid second part according to any aspect of the present invention in the second barrel thereof and also comprising the further components of the aspects of the invention as disclosed herein.

For medical applications such as bone cement and dentistry to which the compositions of the invention are mainly directed the composition is biocompatible and in particular hardens to a solid cement or adhesive that is biocompatible in situ. Accordingly, the composition of the invention finds particularly advantageous utility as a medical implant material such as a bone cement or a solid effective in dental applications. Accordingly, the multi-part composition is typically a bone cement composition or dental composition.

According to a further aspect of the present invention there is provided a medical implant material produced from mixing a multi-part acrylic composition according to the present invention.

According to a still further aspect of the present invention there is provided a multi-part composition according to any aspect of the present invention for use in surgery, more particularly for use in the treatment of human or animal bone or teeth.

According to a still further aspect of the present invention there is provided a multi-part composition according to any aspect of the present invention for use in the replacement or partial replacement of human or animal bone.

According to a still further aspect of the present invention there is provided a multi-part composition according to any aspect of the present invention for use dentistry, more particularly in the treatment of human teeth or animal teeth or for use in veterinary surgery, more particularly, for use in the treatment of hoof, nail or horn.

According to a still further aspect of the present invention there is provided a multi-part composition according to any aspect of the present invention for use in the replacement or partial replacement of human teeth or animal teeth, hoof, nail or horn.

A general procedure for mixing the parts of the hardenable composition of the invention is described as follows: Before mixing, the two components are equilibrated for a suitable period, typically, 1 hour or more at a temperature of 5-40° C., more typically, 10-35° C., most typically, 15-30° C. Liquid first part is mixed with a suitable amount of liquid second part and, if present, any other liquid parts according to the ratios defined herein. Mixing is then carried out at the equilibrated temperature for at least 5, more typically, at least 20, most typically, at least 30 seconds. When the dough time has been reached, the doughed material is packed into place such as moulds preconditioned at an appropriate temperature generally in the range of the equilibration temperatures above and allowed to exotherm and harden. Alternatively, the doughed material may be implanted within some other cavity, such as bone and allowed to exotherm and harden.

The mixing of the two components and subsequent reaction can be carried out at the equilibration temperatures. The skilled person will be aware of the effect of temperature on the dough and set times. Higher mixing temperature leads to shorter dough and set times and vice versa for lower mixing temperature.

Embodiments of the invention will now be described with reference to the accompanying examples:—

EXAMPLES

Characterisation Techniques:

The Z average particle size of the emulsion polymerized acrylic polymer particles was determined using a Malvern Zetasizer nano series S particle size analyzer.

Reduced viscosity (RV, dl/g) was measured in chloroform (1 wt % solution) using an Ubbelohde viscometer type OB at 25° C.

Wt % residual dibenzoyl peroxide content was determined by a titration method.

Brookfield viscometry (BV, Pascal seconds (Pa·s)) was carried out using a Brookfield Viscometer model RVDV-E at 25° C. operating with spindle number 5 and speed 20 rpm, except for examples W to Z for which spindle number 1 was used.

The mean particle size of acrylic polymer beads was determined using a Coulter L5230 laser diffraction instrument.

Dough and set times and maximum exotherm temperature were measured according to BS ISO 5833:2002.

The dough time is considered to be the length of time following the start of mixing for the mixture to achieve a dough-like mass that does not adhere to a gloved finger when gently touched.

The set time is considered to be the time taken to reach a temperature midway between ambient and maximum.

Flexural strength and flexural modulus of the hardenable compositions were determined by a three-point bend test according to ISO 1567:1997. Compressive strength was determined according to ISO 5833:2002.

Example 1

Preparation of Ca. 50% w/w Solids Acrylic Polymer Emulsion of 582 nm Z-Average Particle Size.

600 grams of deionised water is added to a five-liter round bottomed glass flask fitted with a nitrogen inlet, condenser and electrically operated stainless steel paddle stirrer. The water is heated to 80° C. by means of a water bath whilst stirring at 200 revolutions per minute (rpm). A flow of nitrogen is passed through the vapour space of the flask above the surface of the liquid. An emulsified monomer mixture is prepared consisting of 980 grams methyl methacrylate (MMA), 0.5 grams of 1-dodecanethiol, 5.0 grams of sodium lauryl sulphate and 300 grams of deionised water. This mixture is stirred for 60 minutes prior to and throughout addition to keep it emulsified.

With the temperature of the water at 80° C., a polymer seed (Stage 1) is prepared by adding 20 grams of methyl methacrylate to the flask followed by a solution of 0.3 grams potassium persulphate in 10 milliliters of deionised water and react at 80° C. for 1 hour.

The core is then grown over the polymer seed particles (Stage 2) by firstly adding 10 milliliters of a 2% w/w solution of potassium persulphate in deionised water to the flask followed by continuous addition of 300 grams of the emulsified monomer mixture over approximately 30 minutes using a peristaltic pump. The reaction proceeds for a further 15 minutes after the completion of addition of the monomer mixture until the temperature returns to 80° C. This step is then repeated twice.

35.0 grams of 75% active dibenzoyl peroxide (BPO) are dissolved in the remaining 380 grams of emulsified monomer mixture with stirring for 45 minutes.

The BPO-containing shell is then grown over the core (Stage 3) by firstly adding 10 milliliters of a 2% w/w solution of potassium persulphate in deionised water to the flask followed by continuous addition of the emulsified monomer mixture containing added BPO over approximately 20 minutes using a peristaltic pump. The reaction proceeds for a further fifteen minutes after all the monomer mixture has been added until the temperature has returned to 80° C.

The resultant acrylic polymer emulsion is then cooled to below 40° C. and filtered through a 150 µm screen.

The resultant acrylic polymer emulsion has a solids content of 48.0% w/w, reduced viscosity of 1.94 dl/g, Brookfield Viscosity of 0.021 Pa·s, residual dibenzoyl peroxide of 2.28% w/w and a Z-average particle size of 582 nm.

Example 2

Preparation of Acrylic Polymer Beads Containing Encapsulated and Adsorbed X-Ray Opacifying Filler for Use in Preparing a Hardenable Composition.

The preparation of acrylic beads containing encapsulated and adsorbed barium sulphate is carried out in a two-step process. Firstly, the barium sulphate (from Sachtleben Chemie GmbH) is dispersed in a syrup prepared from dissolving polymer in monomer, followed by the transformation of the dispersion into barium sulphate-filled acrylic polymer beads by suspension polymerization.

A 20% wt solution of poly(methyl methacrylate-co-N,N'-dimethylamino ethyl methacrylate) (poly(MMA-co-DMAEMA) (RV=0.5 dl/g) in MMA is prepared by dissolving 100 g of the poly(MMA-co-DMAEMA) in 400 g of MMA at room temperature. 300 g of this syrup is transferred to a 2 liter glass flask equipped with stainless steel anchor-type stirrer and 400 g of barium sulphate (medical grade) is added. The flask and contents are weighed and the weight recorded. The mixture is then stirred at room temperature for 5 hours at a stirrer speed of 1500-1900 rpm. 300 g of MMA monomer is then added and stirring is continued at 1500 rpm for a further 40 minutes. The flask is reweighed and the reduction in weight due to evaporation of MMA calculated. The calculated amount of evaporated MMA is then added to the flask along with 10 g of benzoyl peroxide (75% concentration) initiator and the mixture is stirred at 1500 rpm for 15 minutes at room temperature. This forms the organic phase of the suspension polymerization.

Separately, the aqueous phase of the suspension polymerization is prepared by adding 2000 ml of deionized water and 8 g of hydroxyethyl cellulose powder (Natrosol HEC 250HR from Aqualon Ltd) to a 5 liter glass flask containing a stainless steel anchor-type stirrer. The flask contents are stirred at 400 rpm and heated to 40° C. to dissolve the hydroxyethyl cellulose. The organic phase containing the barium sulphate dispersed in a monomer/polymer syrup is then added and the contents of the reactor flask heated to 82° C. using a water bath. The polymerization is continued at 82° C. until the reactor contents experience an exotherm, typically to approximately 90-92° C. The reactor flask is then cooled and the resultant acrylic polymer beads containing encapsulated and adsorbed barium sulphate are filtered, washed with deionized water, dried in an air circulating oven overnight at 50° C. and sieved through a 300 µm screen. The resultant product has an ash content of 40.2% w/w, residual benzoyl peroxide content of 1.1% w/w, mean particle size of 75 µm. The ash content represents the amount of encapsulated and adsorbed barium sulphate in the acrylic polymer beads.

Example 3

Use of the Acrylic Polymer Emulsion of Example 1 and Acrylic Polymer Beads Containing Encapsulated and Adsorbed X-Ray Opacifying Filler of Example 2 to Prepare Firstly a Liquid First Part and then a Hardenable Composition.

A liquid first part is prepared as follows: To a 250 ml polypropylene beaker equipped with electric stirrer motor and stainless steel paddle stirrer is added 70.0 g of the acrylic bead polymer containing encapsulated and adsorbed barium sulphate of example 2. Stirring is commenced at 100 rpm and 30.0 g of the acrylic polymer emulsion of example 1 is added over 60 to 90 seconds. The stirrer speed is then increased to 600-1000 rpm and mixing is continued for a further 3 to 5 minutes until a uniform liquid mixture is obtained. The Brookfield viscosity is 15.2 Pa·s. In contrast, the Brookfield viscosity of a liquid first part prepared in a similar way but adding the barium sulphate as a separate powder component to the liquid first part (comparative example 1) cannot be measured as the mixture is semi-solid in consistency.

The liquid second part is prepared by dissolving 10 g of a poly(MMA-co-DMAEMA) copolymer (free of residual initiator, RV=0.50 dl/g) and 10.0 g of a higher molecular weight poly(MMA-co-DMAEMA) copolymer (free of residual initiator, RV=1.52 dl/g) in a mixture of 78.4 g of MMA monomer (stabilised with 60 ppm hydroquinone (HQ) inhibitor) and 1.6 g of N,N-dimethyl-para-toluidine (DMPT) accelerator. The Brookfield viscosity of the resultant syrup is 1.42 Pa·s.

The preparation of a hardenable composition from the liquid first part and the liquid second part is described as follows: Before mixing, the two components are equili-

Comparative Example 2

Example 3 is repeated except that the liquid first part does not contain any barium sulphate. Instead, the same amount of barium sulphate as example 3 is dispersed in the liquid second part. This is prepared by firstly dissolving 12.0 g of poly(MMA-co-DMAEMA) copolymer (free of residual initiator, RV=0.50 dl/g) in 47.52 g of MMA monomer (stabilised with 60 ppm hydroquinone (HQ) inhibitor) and 0.48 g of N,N-dimethyl-para-toluidine (DMPT) accelerator in a glass flask equipped with stirrer. The required amount of barium sulphate (40.0 g) is then added with stirring at 500-600 rpm and left for 1 hour to disperse the barium sulphate in the monomer/polymer syrup.

Comparative Example 3

This describes the preparation of a hardenable composition that has the same components as example 3 but without the addition of barium sulphate in either liquid first part or liquid second part to show the deleterious impact its addition has on mechanical properties.

TABLE 1

|  | Description | Viscosity comparison | Dough time mins:secs | Set time mins:secs | Exotherm temperature (° C.) | Flexural strength (MPa) | Flexural Modulus (GPa) | Compressive Strength (MPa) |
| --- | --- | --- | --- | --- | --- | --- | --- | --- |
| Example 3 | Encapsulated and adsorbed barium sulphate | Liquid first part = 15.2 Pa · s Liquid second part = 1.42 Pa · s | 1:00 | 8:54 | 89.5 | 59.6 | 2.15 | 69.3 |
| Comparative example 1 | Barium sulphate dispersed as powder component of liquid first part | Liquid first part = >90 Pa · s Liquid second part = 1.42 Pa · s | 3:10 | 16:34 | 87.8 | 45.6 | 1.52 |  |
| Comparative example 2 | Barium sulphate dispersed in liquid second part | Liquid first part = 1.92 Pa · s Liquid second part = 2.50 Pa · s | 0:55 | 11:00 | 88.5 | 45.0 | 1.69 |  |
| Comparative example 3 | No barium sulphate in either liquid first part or second part | Liquid first part = 1.92 Pa · s Liquid second part = 1.42 pa · s | 1:00 | 13:30 | 87.9 | 65.0 | 2.32 | 66.9 | brated for at least 10 hours in an incubator at 23° C. 14.0 g of liquid first part is placed into a polypropylene beaker followed by 14.0 g of liquid second part. The amount of barium sulphate in the total mixture is 14% w/w. Hand mixing is then carried out at 23° C. for 30 seconds using a metal spatula, whereupon the material is covered and left to stand. Periodically, the material is assessed for initial mix consistency and the dough and set times determined. The exotherm temperature is also measured by use of a thermocouple embedded in the middle of the curing mass. For preparing specimens for mechanical testing, doughed material is packed into moulds preconditioned at 23° C. and allowed to harden.

Table 1 shows the resultant properties.

Comparative Example 1

Example 3 is repeated except that the acrylic polymer beads containing encapsulated and adsorbed barium sulphate are replaced with poly(methyl methacrylate) (PMMA) beads of equivalent particle size and residual peroxide, and the barium sulphate is added as a separate powder component during the preparation of a liquid first part. The Brookfield viscosity of the liquid first part cannot be measured as the mixture is semi-solid in consistency.

It can be seen that the main advantage of encapsulating the barium sulphate X-ray opacifying filler in the acrylic polymer beads prior to preparing the liquid first part (example 3) is to overcome the reduction in performance observed by incorporating the barium sulphate as a separate component to either the liquid first part (comparative example 1) or second part (comparative example 2). In fact, the results show that the performance of example 3 is approaching that of a hardenable composition prepared without adding barium sulphate (comparative example 3).

Example 4

Repeat of Example 3 Except Barium Sulphate is Replaced with Zirconium Dioxide as X-Ray Opacifying Filler.

To demonstrate that other X-ray opacifying fillers can be used, example 3 was repeated using zirconium dioxide (particle size 5 µm, 99% purity, from Sigma-Aldrich) instead of barium sulphate. The Brookfield viscosity of the resultant liquid first part is 1.22 Pa·s. The mechanical properties of the resultant material were measured and found to be: flexural strength=53.0 MPa and flexural modulus=2.08 GPa.

Comparative Example 4

Example 4 is repeated except that the acrylic polymer beads containing encapsulated zirconium dioxide are replaced with poly(methyl methacrylate) (PMMA) beads of equivalent particle size and residual peroxide, and the zirconium dioxide is added as a separate powder component during the preparation of a liquid first part. The Brookfield viscosity of the liquid first part is 2.46 pa·s. The mechanical properties of the resultant material are flexural strength=42.5 MPa and flexural modulus=2.10 GPa.

It can be seen that the mechanical properties of example 4 which contain acrylic bead polymer containing encapsulated zirconium dioxide are superior to the mechanical properties of comparative example 4 which involves adding the zirconium dioxide as a separate powder ingredient. The Brookfield viscosity of example 4 is also advantageously lower than that of comparative example 4.

Example 5

A first component is prepared by mixing 16.8 g of the acrylic bead polymer containing encapsulated and adsorbed barium sulphate of example 2 with 3.2 g of an aqueous solution containing Tween 80 and sodium carboxymethyl cellulose (prepared by dissolving 3 g Tween 80 (from Sigma-Aldrich) and 2.0 g sodium carboxymethyl cellulose (C300P from Hoechst) in 100 g deionised water). The amount of barium sulphate in the acrylic bead polymer is 40% wt. A second component is a 15% w/w syrup of PMMA homopolymer in MMA monomer prepared by dissolving 15.0 g of a PMMA bead polymer (free of residual initiator and with molecular weight Mw 426,700 daltons and reduced viscosity of 2.8 dl/g) in a mixture of 84.0 g of MMA monomer (stabilised with 60 ppm hydroquinone (HQ) inhibitor) and 1.0 g of N,N-dimethyl-para-toluidine (DMPT) accelerator.

The preparation of a hardenable composition from the first and second components is described as follows: Before mixing, the two components are equilibrated for at least 10 hours in an incubator at 23° C. 14.0 g of the first component is placed into a polypropylene beaker followed by 14.0 g of the second component. The amount of barium sulphate in the total mixture is therefore 13.4% w/w. Hand mixing is then carried out at 23° C. for 30 seconds using a metal spatula, whereupon the material is covered and left to stand. Periodically, the material is assessed for initial mix consistency and the dough and set times determined. The exotherm temperature is also measured by use of a thermocouple embedded in the middle of the curing mass. For preparing specimens for mechanical testing, doughed material is packed into moulds preconditioned at 23° C. and allowed to harden.

The mechanical properties of the resultant material are flexural strength=50.2 MPa and flexural modulus=2.15 GPa.

Comparative Example 5

Example 5 is repeated except that the barium sulphate is added as a separate powder ingredient during the preparation of a first component. The mechanical properties of the resultant material are flexural strength=39.2 MPa and flexural modulus=1.45 GPa.

It can be seen that the mechanical properties of example 5 which contain acrylic bead polymer containing encapsulated and adsorbed barium sulphate are superior to the mechanical properties of comparative example 5 which involves adding the barium sulphate as a separate powder ingredient.

Example 6

A first component is prepared by mixing 10.0 g of a crosslinked acrylic bead polymer containing encapsulated and adsorbed barium sulphate (prepared according to example 2 except that the monomer mixture used has the composition methyl methacrylate (MMA)/ethylene glycol dimethacrylate (EGDMA) 98.85/1.15% w/w instead of 100% MMA) with 10.0 g of a 20% solution of poly(MMA-co-DMAEMA) copolymer (free of residual initiator, RV=0.50 dl/g) in MMA monomer (stabilised with 60 ppm hydroquinone (HQ) inhibitor) and 0.05 g of benzoyl peroxide (75% concentration). The amount of barium sulphate in the first component is 20% w/w.

A second component is prepared by mixing 10.0 g of a crosslinked acrylic bead polymer containing encapsulated and adsorbed barium sulphate (prepared according to example 2 except that the monomer mixture used has the composition methyl methacrylate (MMA)/ethylene glycol dimethacrylate (EGDMA) 98.85/1.15% w/w instead of 100% MMA) with 10.0 g of a 20% solution of poly(MMA-co-DMAEMA) copolymer (free of residual initiator, RV=0.50 dl/g) in MMA monomer (stabilised with 60 ppm hydroquinone (HQ) inhibitor) and 0.04 g of N,N-dimethyl-para-toluidine (DMPT) accelerator. The amount of barium sulphate in the second component is 20% w/w.

The preparation of a hardenable composition from the first and second components is described as follows: Before mixing, the two components are equilibrated for at least 10 hours in an incubator at 23° C. 20.0 g of the first component is placed into a polypropylene beaker followed by 20.0 g of the second component. Hand mixing is then carried out at 23° C. for 30 seconds using a metal spatula, whereupon the material is covered and left to stand. For preparing specimens for mechanical testing, doughed material is packed into moulds preconditioned at 23° C. and allowed to harden.

The mechanical properties of the resultant material were measured and found to be: flexural strength=56.3 MPa and flexural modulus=2.75 GPa.

Comparative Example 6

Example 6 is repeated except that the barium sulphate is added as a separate powder ingredient during the preparation of the first and second components. The amount of barium sulphate in the first and second components is 20% w/w.

The mechanical properties of the resultant material were measured and found to be: flexural strength=44.0 MPa and flexural modulus=2.73 GPa.

It can be seen that the mechanical properties of example 6 which contain acrylic bead polymer containing encapsulated and adsorbed barium sulphate are superior to the mechanical properties of comparative example 6 which involves adding the barium sulphate as a separate powder ingredient.

Example 7

A liquid first part is prepared by mixing 9.33 g of acrylic bead polymer containing 30% wt of encapsulated and adsorbed barium sulphate synthesised according to the method of example 2 and 10.67 g of MMA monomer (stabilised with 60 ppm hydroquinone (HQ) inhibitor) for 30 minutes at 23° C.

A liquid second part is prepared by mixing 9.33 g of acrylic bead polymer containing 30% wt of encapsulated and adsorbed barium sulphate synthesised according to the method of example 2 and 10.67 g of MMA monomer (stabilised with 60 ppm hydroquinone (HQ) inhibitor) for 30 minutes at 23° C., whereupon 0.04 g of N,N-dimethyl-paratoluidine (DMPT) accelerator is then added and mixing is continued for a further 5 minutes.

The Brookfield viscosity of both the liquid first part and liquid second part measured immediately after preparation is 5.20 Pa·s.

The preparation of a hardenable composition is carried out immediately after the preparation of the liquid first part and the liquid second part. Thus, 14.0 g of liquid first part is placed into a polypropylene beaker followed by 14.0 g of liquid second part. Hand mixing is then carried out at 23° C. for 30 seconds using a metal spatula, whereupon the material is covered and left to stand. Periodically, the material is assessed for initial mix consistency and the dough and set times determined. The exotherm temperature is also measured by use of a thermocouple embedded in the middle of the curing mass. For preparing specimens for mechanical testing, doughed material is packed into moulds preconditioned at 23° C. and allowed to harden.

The mechanical properties of the resultant material were measured and found to be: flexural strength=59.7 MPa and flexural modulus=2.48 GPa. The amount of barium sulphate in the final hardenable composition is 14% w/w.

Example 8

This example is based on example 3, except that the acrylic polymer emulsion is replaced with an equivalent amount of water, sodium lauryl sulphate and unfilled PMMA beads of mean particle size 75 μm. The details are as follows:

A liquid first part is prepared as follows: To a 250 ml polypropylene beaker equipped with electric stirrer motor and stainless steel paddle stirrer is added 70.0 g of the acrylic bead polymer containing encapsulated and adsorbed barium sulphate of example 2 and 14.8 g of PMMA beads (mean particle size 75 μm and residual benzoyl peroxide 0.23% wt). Stirring is commenced at 100 rpm and a solution of 0.2 g sodium lauryl sulphate in 15.0 g water is added. The stirrer speed is then increased to 300 rpm and mixing is continued for a further 3 to 5 minutes until a uniform paste is obtained with a Brookfield viscosity of >90 Pa·s.

The liquid second part is prepared by dissolving 10 g of a poly(MMA-co-DMAEMA) copolymer (free of residual initiator, RV=0.50 dl/g) and 10.0 g of a higher molecular weight poly(MMA-co-DMAEMA) copolymer (free of residual initiator, RV=1.52 dl/g) in a mixture of 78.4 g of MMA monomer (stabilised with 60 ppm hydroquinone (HQ) inhibitor) and 1.6 g of N,N-dimethyl-para-toluidine (DMPT) accelerator. The Brookfield viscosity of the resultant syrup is 1.42 Pa·s.

The preparation of a hardenable composition from the liquid first part and the liquid second part is described as follows: Before mixing, the two components are equilibrated for at least 10 hours in an incubator at 23° C. 14.0 g of liquid first part is placed into a polypropylene beaker followed by 14.0 g of liquid second part. The amount of barium sulphate in the total mixture is 14% w/w. Hand mixing is then carried out at 23° C. for 30 seconds using a metal spatula, whereupon the material is covered and left to stand and form a dough. For preparing specimens for mechanical testing, doughed material is packed into moulds preconditioned at 23° C. and allowed to harden. The mechanical properties of the resultant material were measured and found to be: flexural strength=50.5 MPa and flexural modulus=1.95 GPa.

Comparative Example 7

Example 8 is repeated except that the acrylic polymer beads containing encapsulated and adsorbed barium sulphate are replaced with PMMA beads of equivalent particle size and residual benzoyl peroxide, and the barium sulphate is added as a separate powder component during the preparation of a liquid first part. The Brookfield viscosity of the liquid first part cannot be measured as the mixture is semi-solid in consistency. The mechanical properties of the resultant material were measured and found to be: flexural strength=33.6 MPa and flexural modulus=1.60 GPa.

Table 2 compares the mechanical properties of example 3 with example 8 and comparative example 7

TABLE 2

| | Description of first component | Flexural strength (MPa) | Flexural Modulus (GPa) |
|---|---|---|---|
| Example 3 | Acrylic polymer beads containing encapsulated and adsorbed barium sulphate plus emulsion polymerized acrylic polymer particles | 59.6 | 2.15 |
| Example 8 | As example 3, except that the acrylic polymer emulsion is replaced with an equivalent amount of water, sodium lauryl sulphate and PMMA beads | 50.5 | 1.95 |
| Comparative example 7 | As example 8 except the barium sulphate is added as a separate component | 33.6 | 1.60 |

Comparing example 8 and comparative example 7 shows that the mechanical properties of the final material are enhanced by the use of acrylic polymer beads containing encapsulated and adsorbed barium sulphate. Additionally, example 3 shows that the mechanical properties can be further enhanced by including emulsion polymerized acrylic polymer particles in the first part Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A hardenable multi-part acrylic composition comprising
a storage stable liquid first part,
a storage stable liquid second part, and optionally, a third or further liquid parts, the parts adapted to form a cement which hardens to a solid upon mixing of the parts together, wherein:
the composition comprises
an acrylic monomer component,
an initiator component,
acrylic polymer particles and
a radiopacifying filler, the initiator component is present in an amount effective to polymerize the acrylic monomer component upon mixing and/or activating the parts together such that at least some of the radiopacifying filler is encapsulated within and/or adsorbed on the acrylic polymer particles in a liquid part.

2. The hardenable multi-part acrylic composition according to claim 1, wherein the acrylic polymer particles comprise two or more sub-populations of acrylic polymer particles.

3. The hardenable multi-part acrylic composition according to claim 1, wherein the acrylic polymer particles with encapsulated and/or adsorbed radiopacifying filler are present in a liquid carrier in the liquid first part and/or liquid second part.

4. The hardenable multi-part acrylic composition according to claim 3, wherein the liquid carrier is water or other liquid, the other liquid comprising a monomer, organic solvent, plasticizer, liquid polymer or diluent.

5. The hardenable multi-part acrylic composition according to claim 4, wherein the liquid carrier is water.

6. The hardenable multi-part acrylic composition according to claim 1, wherein at least some of the radiopacifying filler is encapsulated within and/or adsorbed on the acrylic polymer particles in suspension in a liquid part.

7. The hardenable multi-part acrylic composition according to claim 1, wherein between 20 and 100% w/w of the radiopacifying filler in the composition is encapsulated within and/or adsorbed on acrylic polymer particles.

8. The hardenable multi-part acrylic composition according to claim 1, wherein an overall amount of radiopacifying filler in the hardenable multi-part composition is between 1 and 50% w/w.

9. The hardenable multi-part acrylic composition according to claim 1, wherein one or more sub-population(s) of acrylic polymer particles in the composition have a lower average particle size than an average particle size of sub-population(s) having encapsulated and/or adsorbed radiopacifying filler.

10. The hardenable multi-part acrylic composition according to claim 9, wherein the average particle size of the lower average particle size sub-population is 0.01-30 μm.

11. The hardenable multi-part acrylic composition according to claim 9, wherein lower average particle size sub-populations are kept apart from the monomer so that the lower average particle size sub-population(s) preferentially dissolve in the monomer after mixing thereby preventing or reducing dissolution of the sub-population(s) having encapsulated and/or adsorbed radiopacifying filler.

12. The hardenable multi-part acrylic composition according to claim 9, wherein when bead particles are present, the mean particle size of the lower average particle size sub-population(s) ranges from 1 μm to 30 μm.

13. The hardenable multi-part acrylic composition according to claim 9, wherein the lower average particle size sub-population(s) are emulsion particles.

14. The hardenable multi-part acrylic composition according to claim 9, wherein the average particle size of the sub-population(s) having encapsulated and/or adsorbed radiopacifying filler is in the range from 10 to 1000 μm.

15. The hardenable multi-part acrylic composition according to claim 1, wherein the radiopacifying filler is encapsulated within and/or adsorbed on polymer beads or in two or more bead sub-populations.

16. The hardenable multi-part acrylic composition according to claim 1, wherein substantially all the acrylic monomer component in the composition is present in the liquid second part.

17. The hardenable multi-part acrylic composition according to claim 1, wherein substantially all of the acrylic monomer component and the initiator component are located in separate parts of the multi-part composition so that the part containing the monomer component is storage stable to polymerization.

18. The hardenable multi-part acrylic composition according to claim 1, wherein the radiopacifying filler is only encapsulated within and/or adsorbed on acrylic polymer beads.

19. The hardenable multi-part acrylic composition according to claim 1, wherein the radiopacifying filler is encapsulated and/or adsorbed in only the first part of the composition.

20. The hardenable multi-part acrylic composition according to claim 1, wherein the radiopacifying filler is only encapsulated and/or adsorbed in acrylic polymer beads.

21. The hardenable multi-part acrylic composition according to claim 1, wherein at least 50% w/w of the total encapsulated and/or adsorbed radiopacifying filler in the composition is present in acrylic polymer beads.

22. The hardenable multi-part acrylic composition according to claim 1, wherein radiopacifying fillers comprise at least one of zirconium dioxide, strontium carbonate, powdered tantalum, powdered tungsten, barium sulphate and mixtures thereof.

23. The hardenable multi-part acrylic composition according to claim 1, wherein the radiopacifying fillers are zirconium dioxide, barium sulphate, and mixtures thereof.

24. The hardenable multi-part acrylic composition according to claim 1, wherein the liquid first part comprises acrylic polymer particles present as polymer beads and having encapsulated and/or adsorbed radiopacifying filler, the liquid second part comprises the monomer component, the composition comprises emulsion polymerized acrylic polymer particles and the emulsion polymerized acrylic polymer particles are dispersed in a liquid carrier.

25. The hardenable multi-part acrylic composition according to claim 24, wherein the liquid part containing the acrylic polymer particles and encapsulated and/or adsorbed radiopacifying filler further contains the emulsion polymerized acrylic polymer particles, the emulsion polymerized particles in the liquid carrier are in the form of an acrylic polymer emulsion dispersion and the liquid carrier for the acrylic polymer particles, encapsulated and/or adsorbed radiopacifying filler and emulsion polymerized acrylic polymer particles is water.

26. The hardenable multi-part acrylic composition according to claim 24, wherein the liquid carrier forms between 5-90% w/w of the liquid part in which acrylic polymer particle encapsulated and/or adsorbed radiopacifying filler is present.

27. The hardenable multi-part acrylic composition according to claim 1, wherein the amount of acrylic monomer in the hardenable composition ranges from 10% w/w to 70% w/w.

28. The hardenable multi-part acrylic composition according to claim 1, wherein at least 90% w/w of the total radiopacifying filler in the composition is present in the liquid first part.

29. The hardenable multi-part acrylic composition according to claim 1, wherein substantially all of the acrylic monomer component and the radiopacifying filler are located in separate parts of the composition so that the radiopacifying filler is not substantially present in a polymer matrix of the final hardened material.

30. The hardenable multi-part acrylic composition according to claim 1, wherein at least 90% w/w of the total acrylic polymer particles with encapsulated and/or adsorbed radiopacifying filler in the composition are present in the liquid first part.

31. The hardenable multi-part acrylic composition according to claim 1, wherein substantially all of the acrylic monomer component and the acrylic polymer particles with encapsulated and/or adsorbed radiopacifying filler are located in separate parts of the composition so that encapsulated and or adsorbed radiopacifying filler is not released into the monomer component prior to mixing and therefore released radiopacifying filler presence in the polymer matrix of the final hardened material is reduced.

32. The hardenable multi-part acrylic composition according to claim 24, wherein at least 90% w/w of the total emulsion polymerized acrylic particles present in the composition is present in the liquid first part.

33. The hardenable multi-part acrylic composition according to claim 1, wherein a sub-population in the liquid first part includes emulsion polymerized particles and water as a liquid carrier.

34. The hardenable multi-part acrylic composition according to claim 1, wherein the multi-part acrylic composition is a bone cement or dental composition.

35. A liquid composition comprising
a first sub-population of emulsion or non-emulsion polymerized acrylic polymer particles,
optionally at least one further sub-population of emulsion or non-emulsion polymerized acrylic polymer particles,
a polymerization initiator in the liquid composition at a level sufficient to cause the liquid composition to harden upon contact with a reactive monomer liquid, and
a radiopacifying filler encapsulated and/or adsorbed in the first sub-population of acrylic polymer particles.

36. The hardenable multi-part acrylic composition according to claim 13, wherein when emulsion particles, a Z-average particle size of the lower average particle size sub-population(s) ranges from 0.01 to 2 µm.

37. A method of producing a hardenable multi-part acrylic composition according to claim 1 comprising the steps of:
(a) producing a storage stable liquid first part and a storage stable liquid second part according to claim 1;
(i) wherein step (a) comprises the step of polymerizing an acrylic monomer composition to form acrylic polymer particles wherein the polymerisation is carried out in the presence of radiopacifying filler to thereby encapsulate the radiopacifying filler in acrylic polymer particles.

38. A syringe or caulking gun having at least two barrels comprising the liquid first part according to claim 1 in a first barrel thereof and a liquid second part according to claim 1 in the second barrel thereof.

39. A bone cement composition or dental composition according to claim 1.

40. The hardenable multi-part acrylic composition according to claim 4, wherein the liquid carrier for the acrylic polymer particles and encapsulated and/or adsorbed radiopacifying filler is other than monomer.

41. The hardenable multi-part acrylic composition according to claim 4, wherein the liquid carrier for the acrylic polymer particles and encapsulated and/or adsorbed radiopacifying filler is a substantially non-solvating carrier for the acrylic polymer particles with encapsulated and/or adsorbed radiopacifying filler.

42. The hardenable multi-part acrylic composition according to claim 1, wherein a further sub-population in the liquid first part includes emulsion polymerised particles and the liquid carrier is the liquid carrier for the emulsion of emulsion polymerized particles.

* * * * *